(12) United States Patent
High et al.

(10) Patent No.: US 10,448,823 B2
(45) Date of Patent: Oct. 22, 2019

(54) APPARATUS AND METHODS FOR TESTING VISUAL FUNCTION AND FUNCTIONAL VISION AT VARYING LUMINANCE LEVELS

(71) Applicants: The Children's Hospital of Philadelphia, Philadelphia, PA (US); The Trustees of the University of Pennsylvania, Philadelphia, PA (US)

(72) Inventors: Katherine A. High, Merion, PA (US); Jean Bennett, Philadelphia, PA (US); Daniel Chung, Philadelphia, PA (US); Albert Maguire, Philadelphia, PA (US); Jennifer Wellman, Philadelphia, PA (US); Sarah McCague, Philadelphia, PA (US); Gregory Podsakoff, Philadelphia, PA (US)

(73) Assignees: The Children's Hospital of Philadelphia, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/662,153

(22) Filed: Jul. 27, 2017

(65) Prior Publication Data
US 2017/0319058 A1    Nov. 9, 2017

Related U.S. Application Data

(63) Continuation of application No. 14/523,439, filed on Oct. 24, 2014, now abandoned.
(Continued)

(51) Int. Cl.
*A61B 3/06* (2006.01)
*A61B 3/00* (2006.01)
(Continued)

(52) U.S. Cl.
CPC ............ *A61B 3/063* (2013.01); *A61B 3/0008* (2013.01); *A61B 3/0041* (2013.01); *A61B 5/11* (2013.01); *A61B 5/72* (2013.01); *A63B 2220/00* (2013.01)

(58) Field of Classification Search
CPC ............................. A61B 3/063; A61B 3/0008
(Continued)

(56) References Cited

U.S. PATENT DOCUMENTS 4,607,923 A    8/1986  Task et al.
4,715,743 A    12/1987 Schmanski
(Continued)

FOREIGN PATENT DOCUMENTS

JP    2010-233978 A    10/2010
JP    2011-115362 A    6/2011
(Continued)

OTHER PUBLICATIONS

Thomas Kuyk, Jeffry Elliott: DVA Journal of Rehabilitation Research and Development vol. 36 No. 4 Oct. 1999 pp. 303-312.*
(Continued)

*Primary Examiner* — James R Greece
(74) *Attorney, Agent, or Firm* — Pillsbury Winthrop Shaw Pittman LLP; Robert M. Bedgood

(57) ABSTRACT

A test of visual function and/or functional vision may be performed at varying luminance levels. A first course may be selected for a subject. A given course may comprise a layout having a beginning point, at least one turn, at least one obstacle, and an ending point. The first course may be illuminated with a first luminance level based on an estimated lower light sensitivity cutoff. The subject may be prompted to perform a first run of the test. The test may comprise, from the beginning point to the ending point, navigating the layout of the first course by walking around
(Continued)

the at least one turn and avoiding the at least one obstacle. A determination may be made as to whether the subject successfully completed the first course based on one or both of speed or accuracy.

66 Claims, 33 Drawing Sheets

Related U.S. Application Data

(60) Provisional application No. 61/895,855, filed on Oct. 25, 2013.

(51) Int. Cl.
*A61B 5/00* (2006.01)
*A61B 5/11* (2006.01)

(58) Field of Classification Search
USPC .................................................. 351/243, 246
See application file for complete search history.

(56) References Cited

U.S. PATENT DOCUMENTS

| | | | |
|---|---|---|---|
| 7,658,494 | B2 | 2/2010 | Shibata et al. |
| 7,857,450 | B1* | 12/2010 | Hofeldt ................ A61B 3/032 351/233 |
| 2003/0157464 | A1 | 8/2003 | Tanassi et al. |
| 2006/0238704 | A1* | 10/2006 | Donnerhacke ......... A61B 3/022 351/200 |
| 2008/0002153 | A1* | 1/2008 | Kanazawa ............. A61B 3/032 351/239 |
| 2010/0280405 | A1 | 11/2010 | Musialik et al. |
| 2011/0267179 | A1 | 11/2011 | Patterson |
| 2012/0050685 | A1 | 3/2012 | Bartlett et al. |
| 2012/0075586 | A1* | 3/2012 | Kirschen ................ A61B 3/028 351/239 |
| 2013/0236866 | A1* | 9/2013 | MaLossi ................ G09B 19/00 434/247 |

FOREIGN PATENT DOCUMENTS

| | | |
|---|---|---|
| WO | 2001/029799 A2 | 4/2001 |
| WO | 2010/115870 A1 | 10/2010 |
| WO | 2012/037019 A1 | 3/2012 |

OTHER PUBLICATIONS

Nau, A.C., Pintar, C., Fisher, C., Jeong, J.H., Jeong, K. A Standardized Obstacle Course for Assessment of Visual Function in Ultra Low Vision and Artificial Vision. J. Vis. Exp. (84), e51205, doi: 10.3791/51205 (2014).*
Black et al Mobility Performance With Retinitis Pigmentosa, Clinical and Experimental Optometry 80.1, Jan.-Feb. 1997 pp. 1-12 (Year: 1997).*
Black, A., et al., Mobility performance with retinitis pigmentosa, Clinical and Experimental Optometry, 1997, 80 (1):1-12.
Colenbrander, MD, Visual functions and functional vision, International Congress Series, 2005, 1282:482-486.
Kuyk, T., et al., Visual Correlates of Mobility in Real World Settings in Older Adults with Low Vision, Optometry and Vision Science, 1998, 75(7):538-547.
Accessible Pedestrian Signals—A Guide to Best Practices [retrieved from internet on May 31, 2019] <URL: https://web.archive.org/web/20110530065957/http://www.apsguide.org/chapter4_arrow.cfm> published on May 30, 2011 as per Wayback Machine.

* cited by examiner

APPARATUS AND METHODS FOR TESTING VISUAL FUNCTION AND FUNCTIONAL VISION AT VARYING LUMINANCE LEVELS

CROSS-REFERENCE TO RELATED APPLICATIONS

This application is a continuation application of U.S. application Ser. No. 14/523,439, filed Oct. 24, 2014, which claims priority to U.S. Provisional Application No. 61/895,855, filed Oct. 25, 2013, all of which applications are expressly incorporated herein by reference in their entirety.

FIELD OF THE DISCLOSURE

The disclosure relates to apparatus and methods for testing visual function and functional vision at varying luminance levels.

SUMMARY

One aspect of the disclosure relates to an apparatus configured for performing a test of visual function and/or functional vision at varying luminance levels. The apparatus may comprise a plurality of courses configured to facilitate performance of the test. A given one of the plurality of courses may comprise a layout having a beginning point, at least one turn, at least one obstacle, and an ending point. Performing the test may comprise: selecting a first course of the plurality of courses for a subject; illuminating the first course with a first luminance level based on an estimated lower light sensitivity cutoff, the estimated lower light sensitivity cutoff being the lowest light sensitivity at which the subject can successfully navigate a preliminary course of the plurality of courses when the estimated lower light sensitivity cutoff is measured; indicating to a subject to perform a first run of the test, the test comprising, from the beginning point to the ending point, navigating the layout of the first course by walking around the at least one turn and avoiding the at least one obstacle; and determining whether the subject successfully completed the first course based on one or both of speed or accuracy, speed describing the time to complete the first course, accuracy describing avoidance of obstacles.

These and other objects, features, and characteristics of the disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure. As used in the specification and in the claims, the singular form of "a", "an", and "the" include plural referents unless the context clearly dictates otherwise.

DETAILED DESCRIPTION

Figure 1:
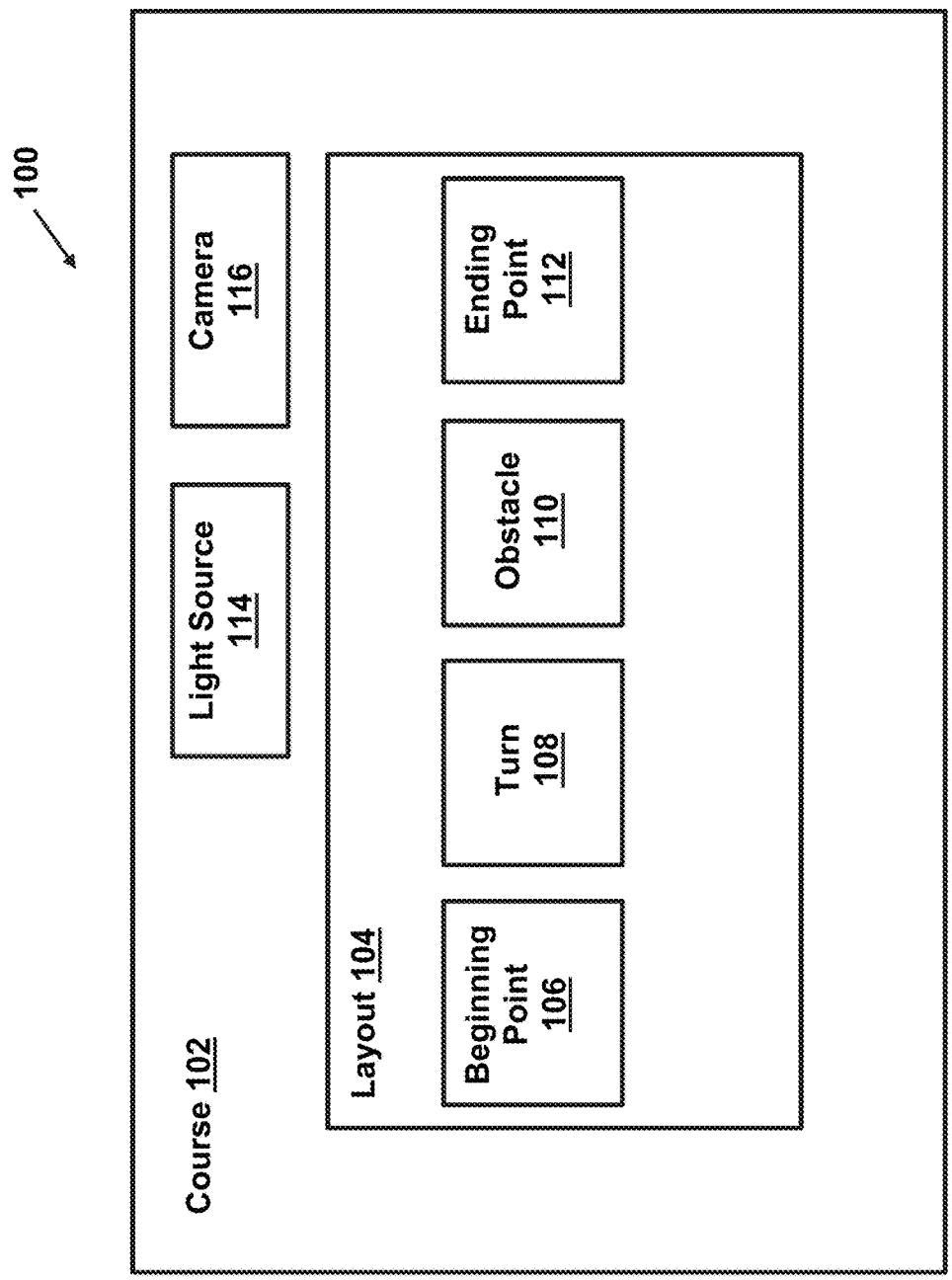
FIG. 1 illustrates an apparatus configured for performing a test of visual function and/or functional vision at varying luminance levels, in accordance with one or more implementations.
Figure 2:
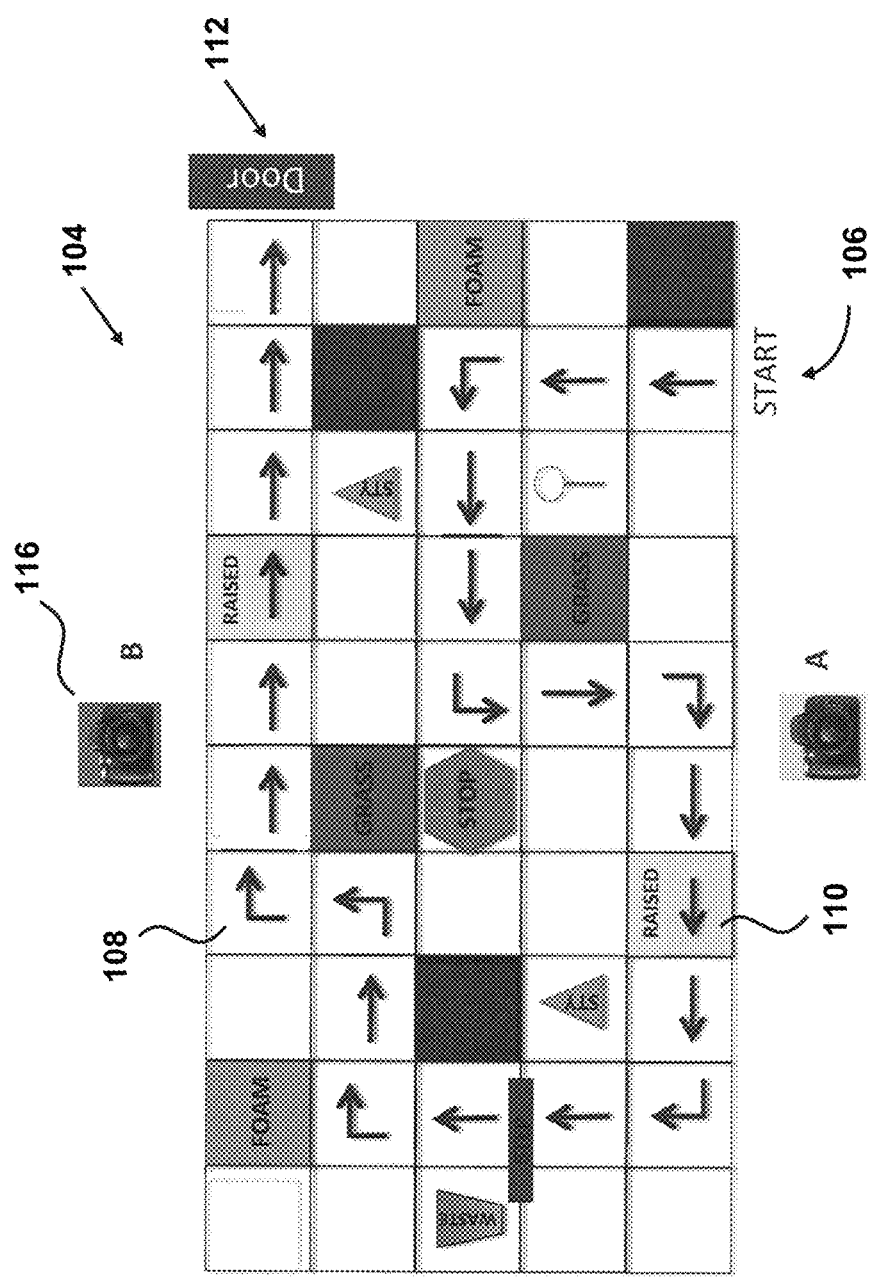
FIGS. 2-13 illustrate exemplary course layouts, in accordance with various implementations.
Figure 3:
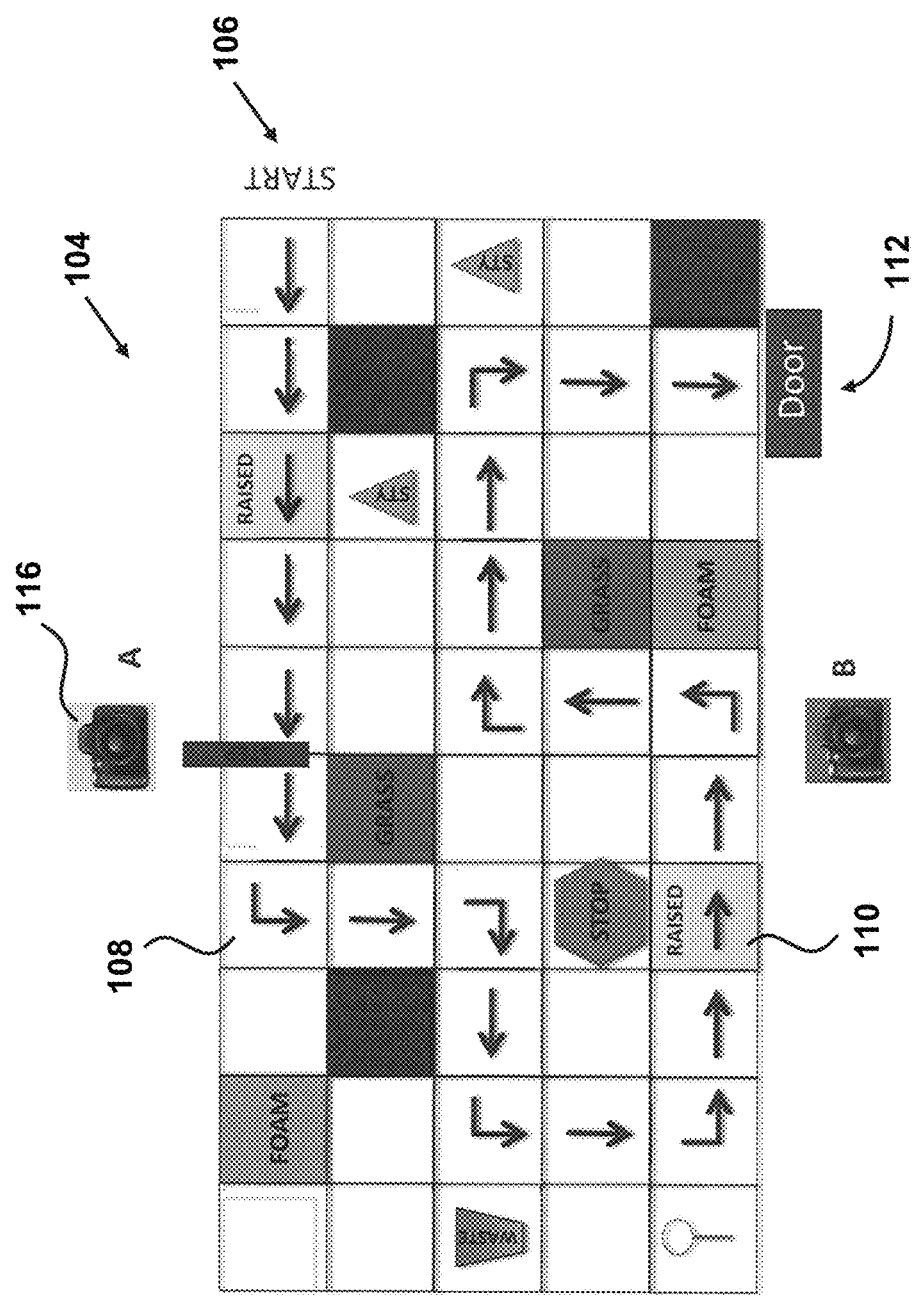
Figure 4:
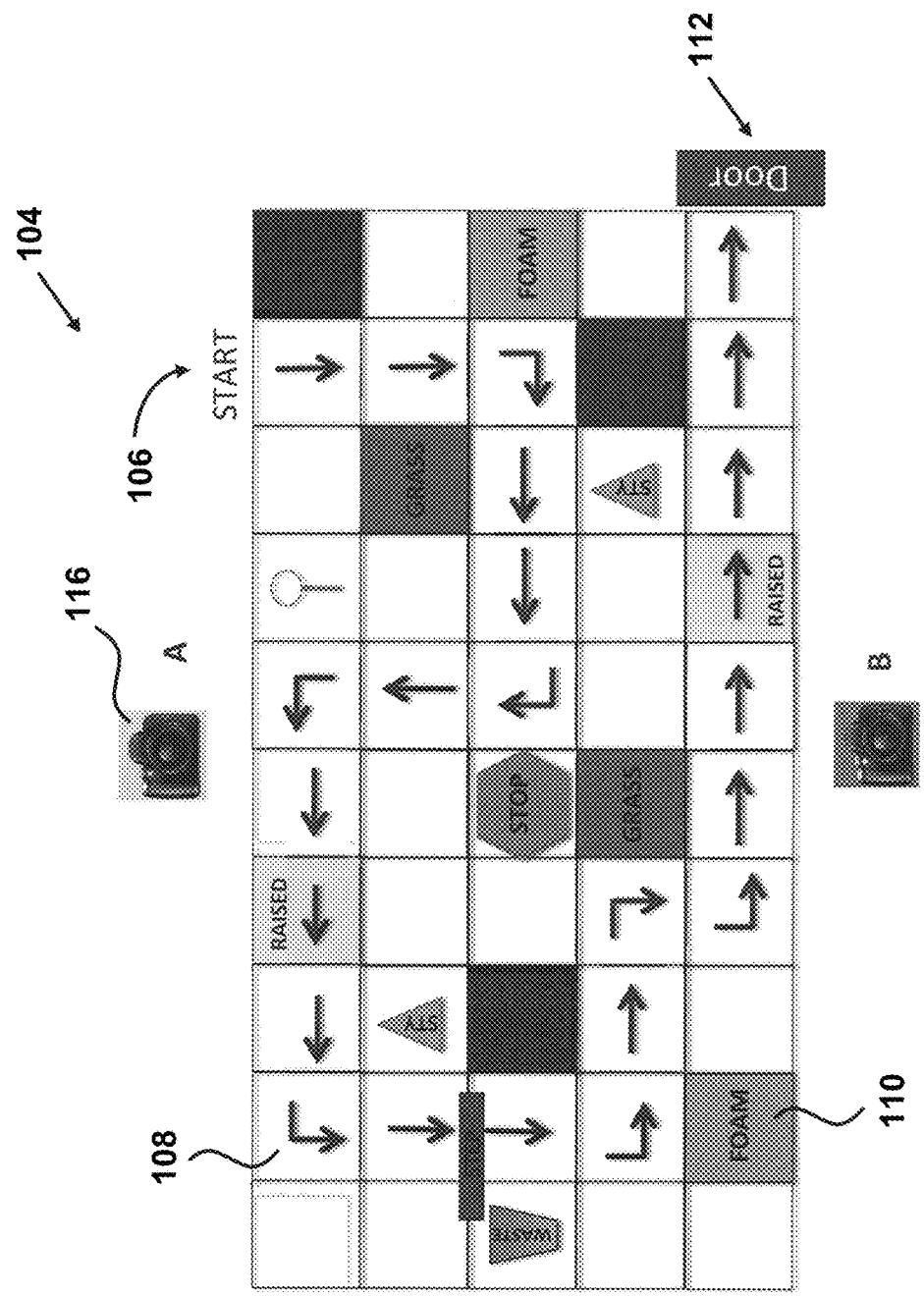
Figure 5:
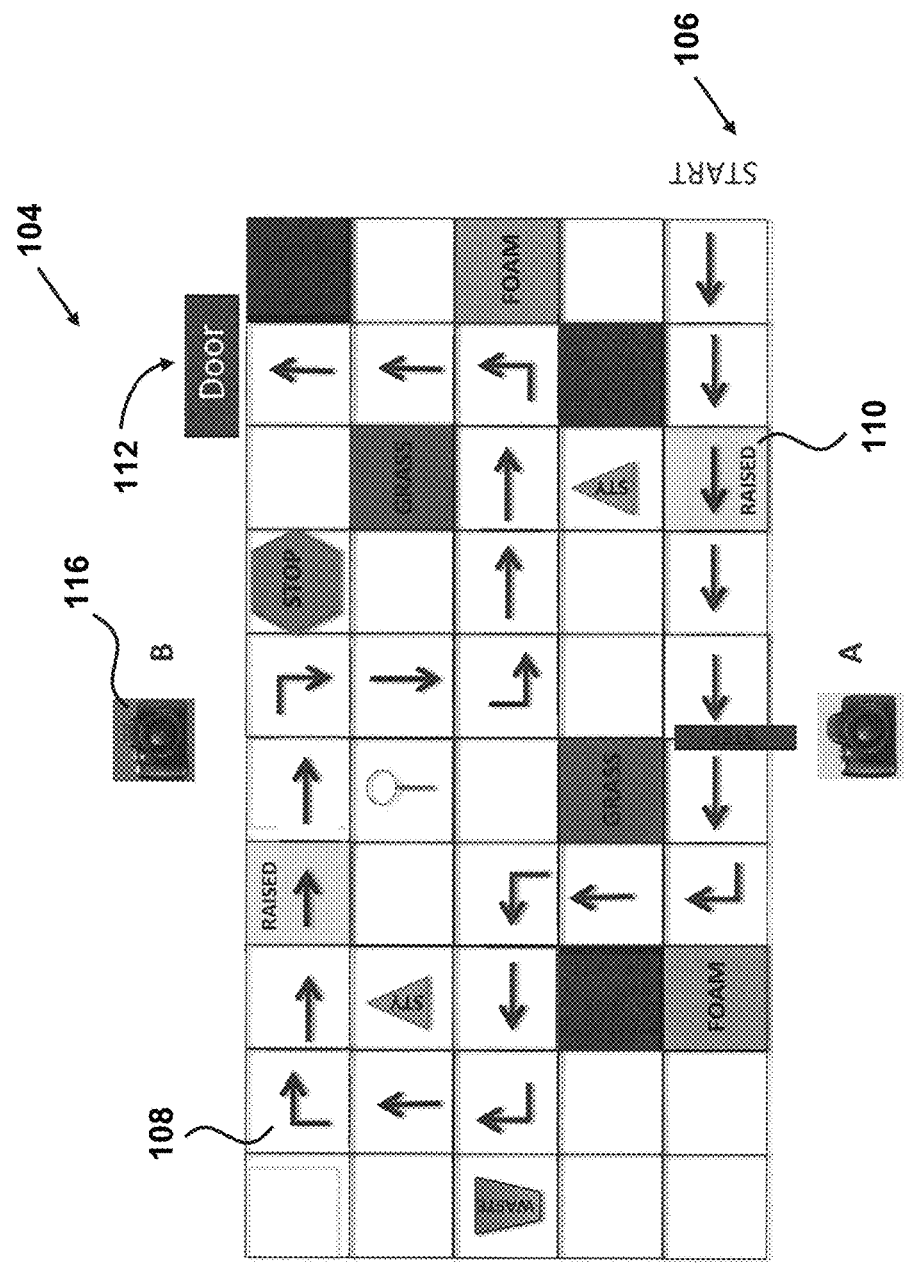
Figure 6:
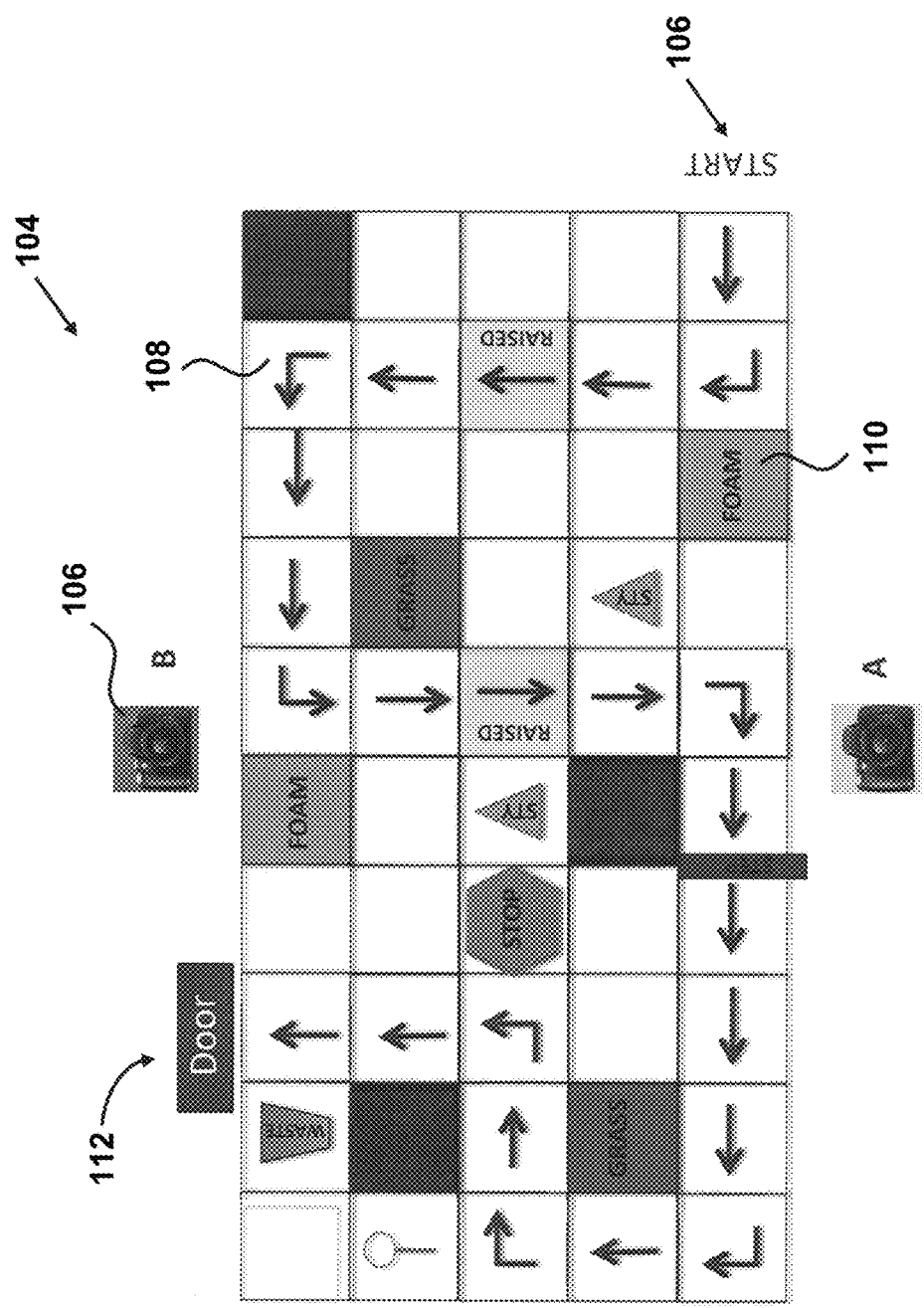
Figure 7:
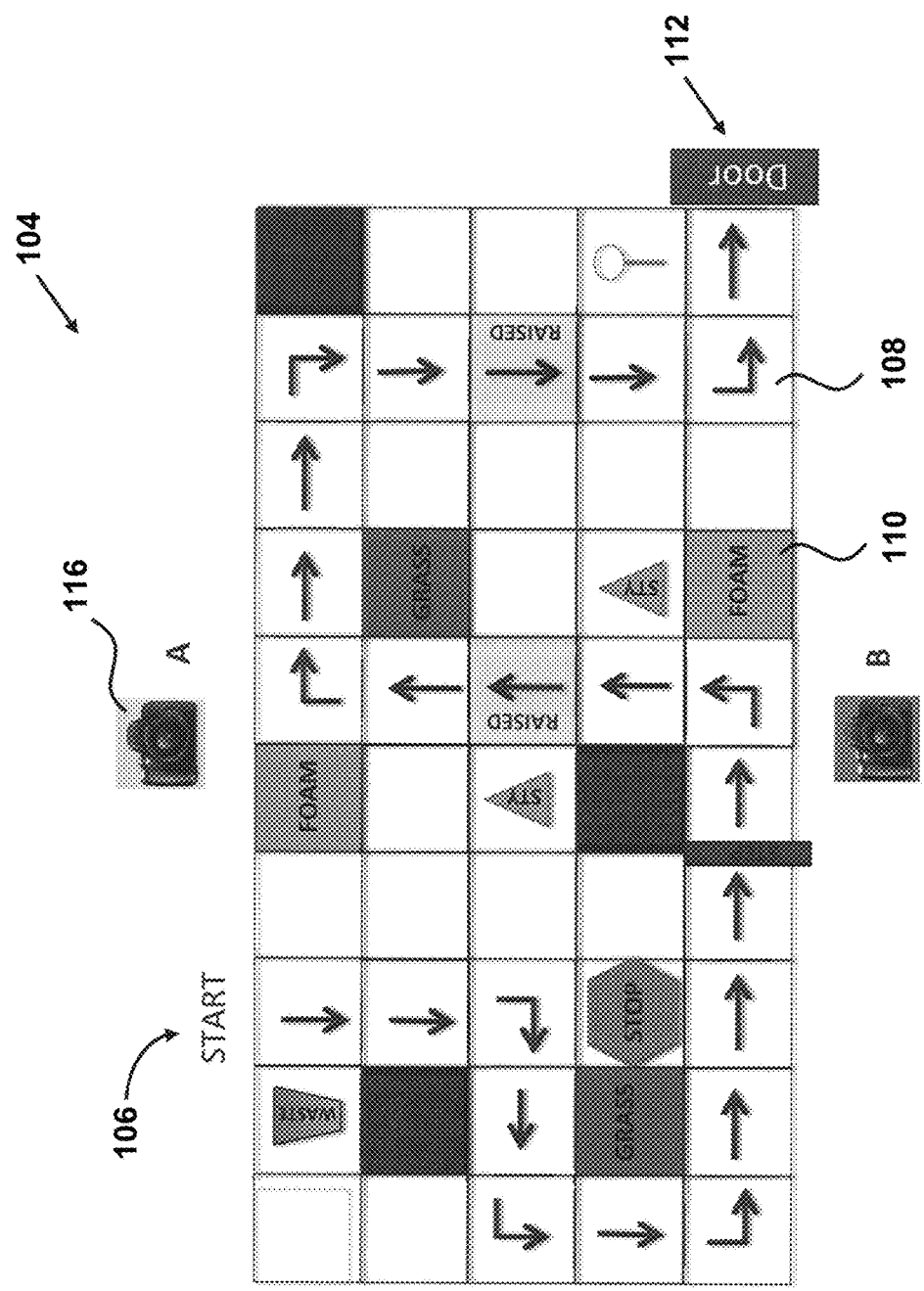
Figure 8:
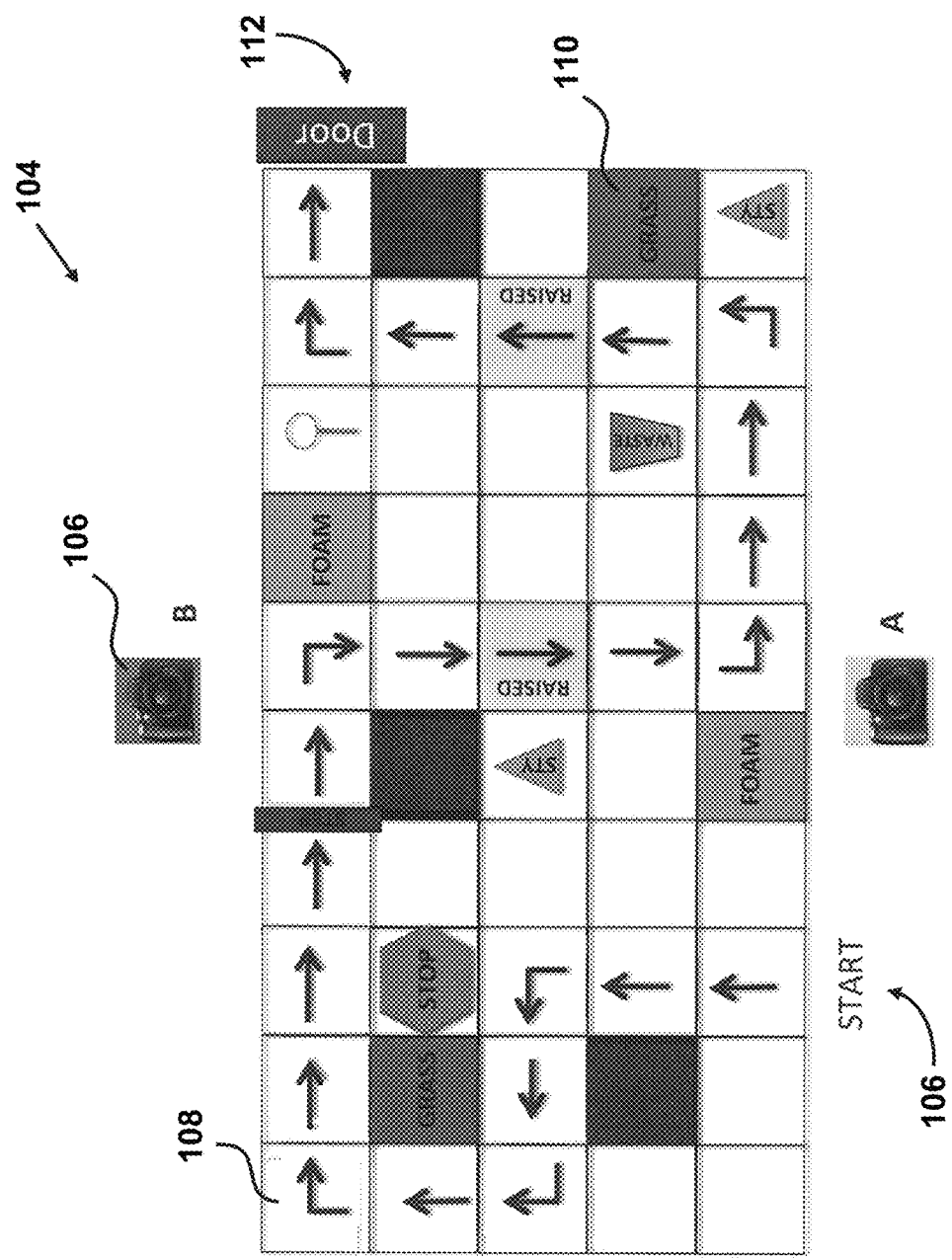
Figure 9:
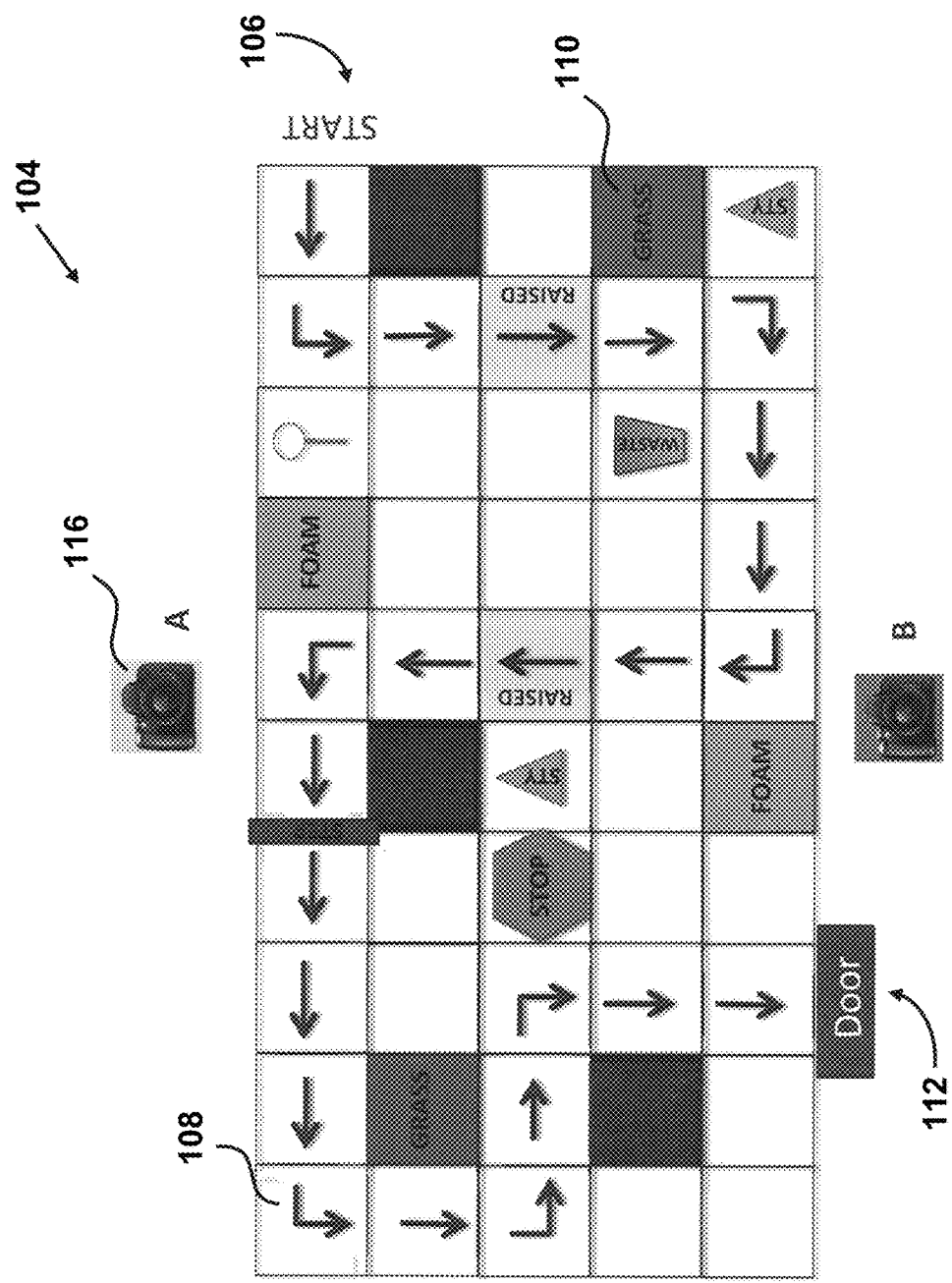
Figure 10:
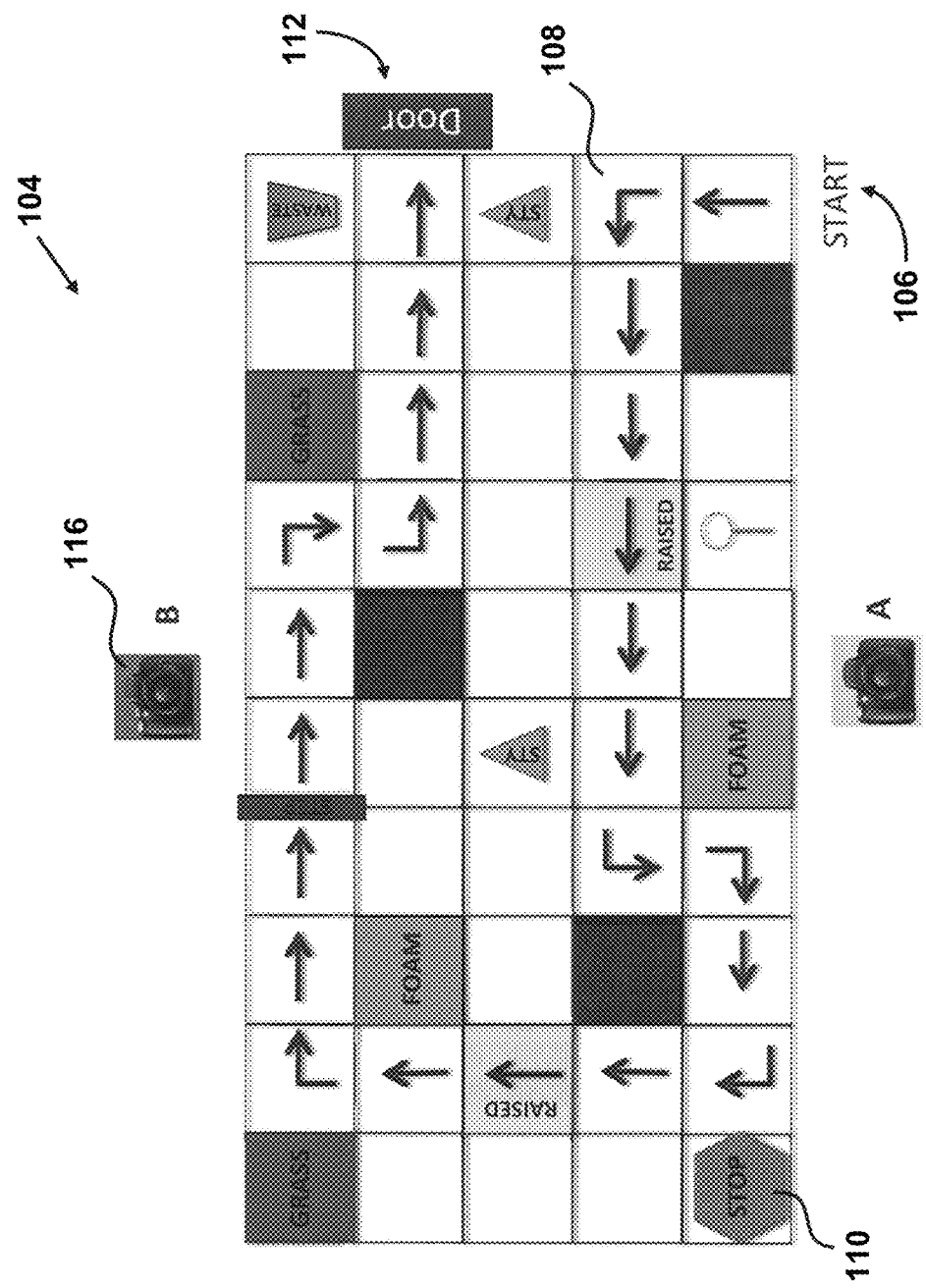
Figure 11:
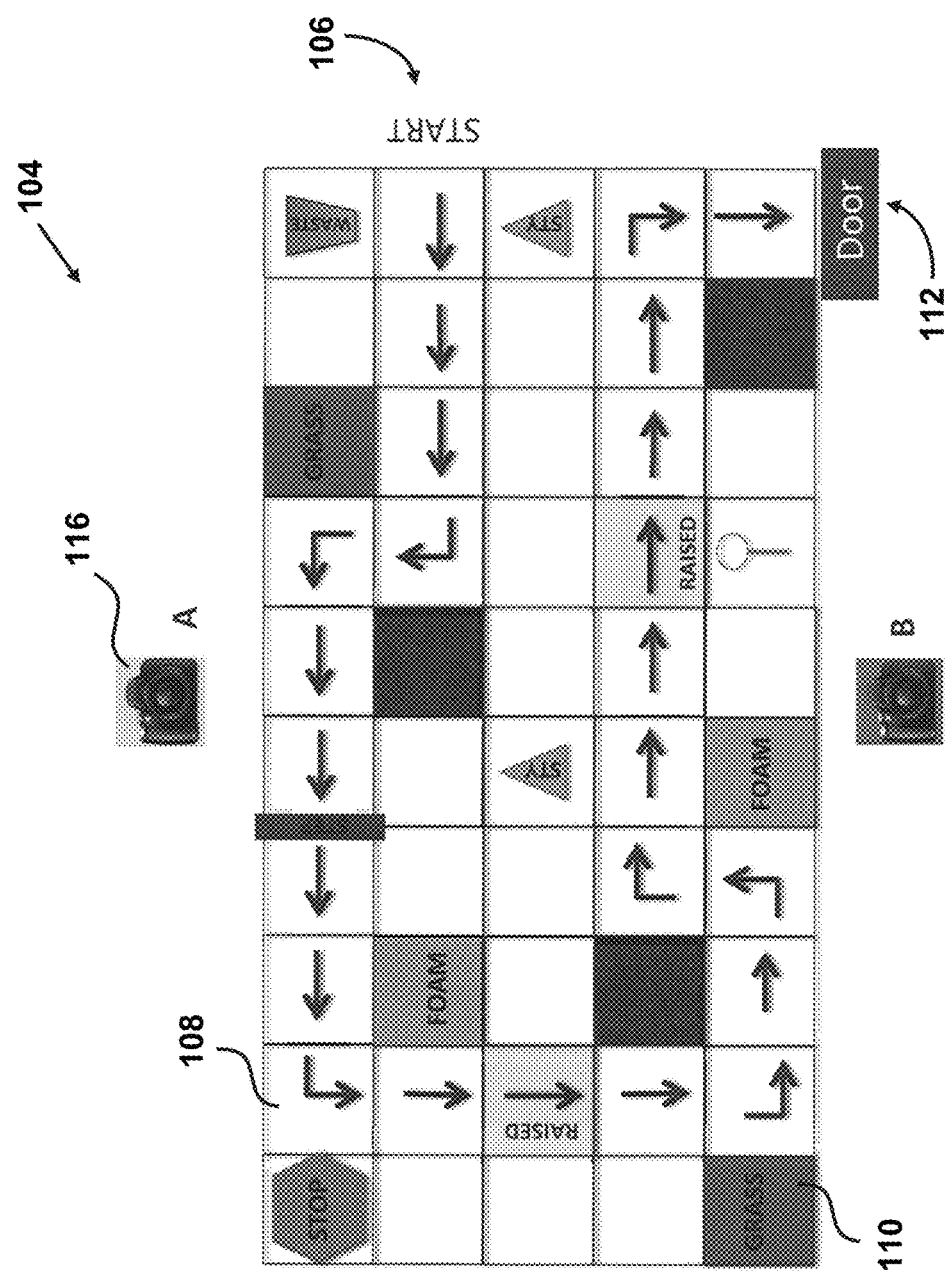
Figure 12:
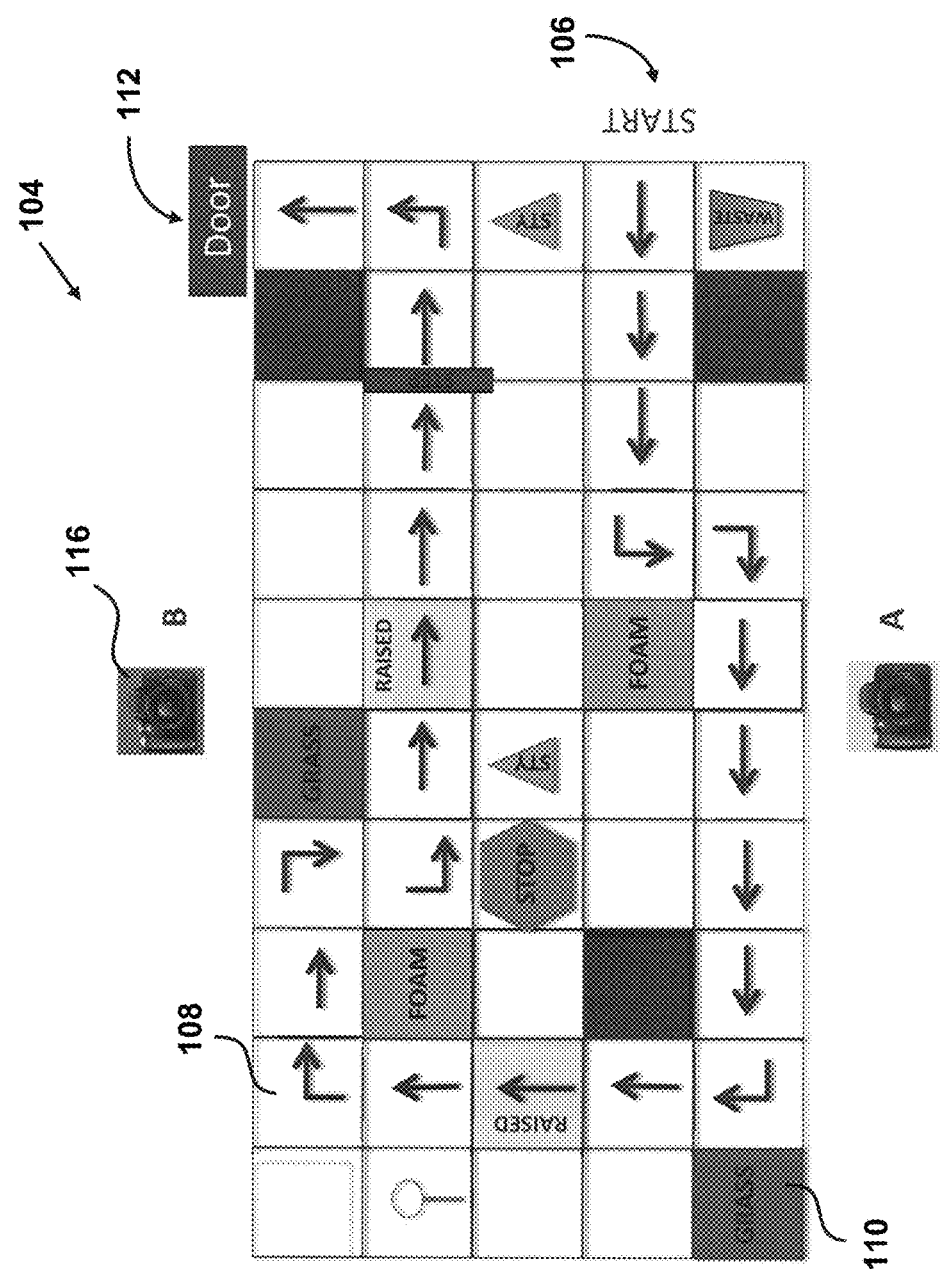
Figure 13:
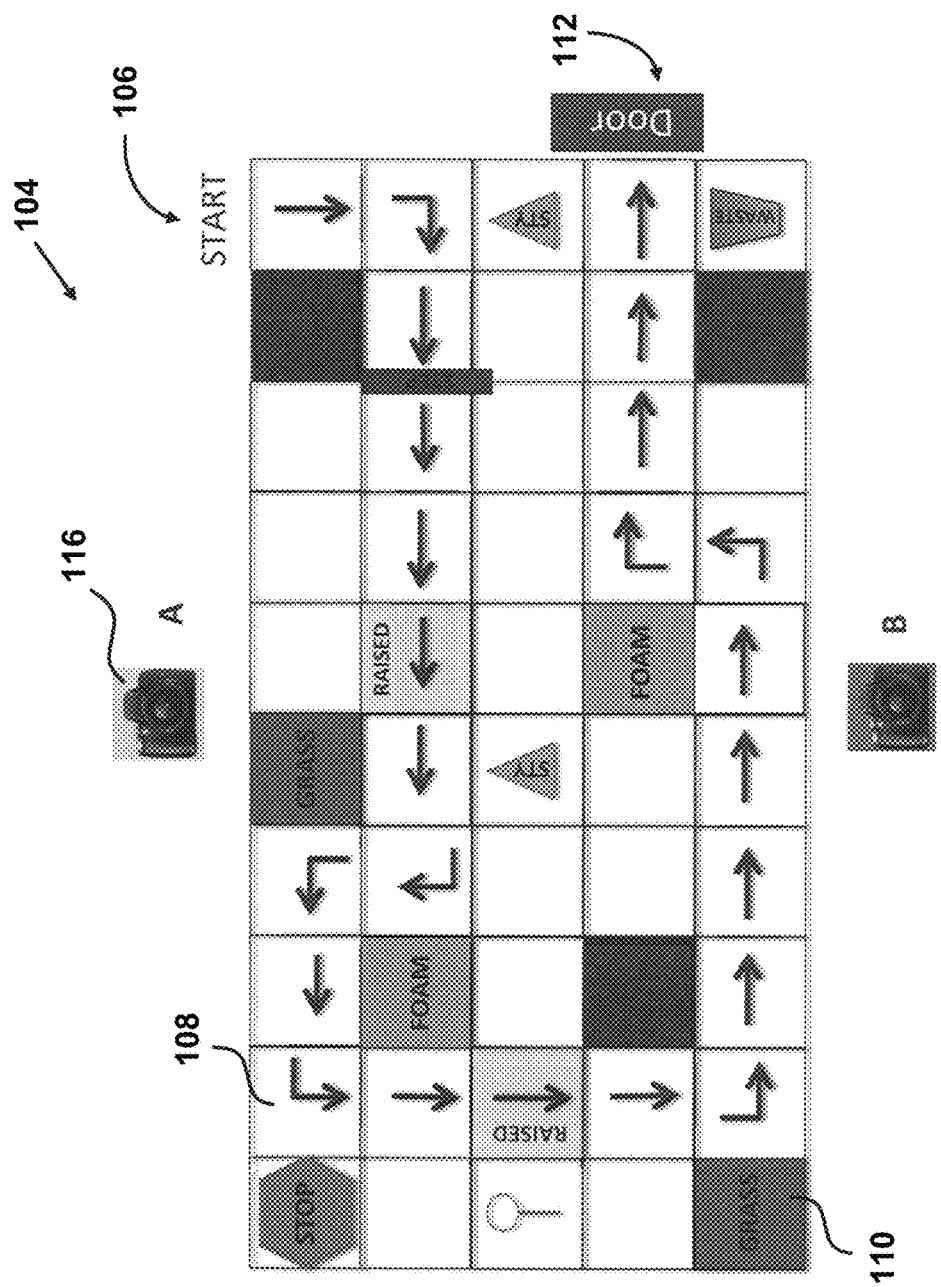

In developing treatments for individuals with low vision, assessment of change in vision may include evaluation of visual function, functional vision, and/or patient-reported outcomes.

Visual function may be described as how the eyes function, which in turn can provide an estimate of functional vision. Visual function can include visual acuity, visual field, contrast sensitivity, color vision and dark adaptation. Each eye can be measured separately for visual function. Non-limiting examples of tests to evaluate visual function include, for example, electroretinograms, which measure retinal response to photic stimulation (electrical response); and pupillometry, which measures transmission of retinal activity to higher visual pathways.

Functional vision may be described as how a person functions or performs in a vision related activity. Such activities include reading, orientation, mobility and navigation, and visual communication and visual occupational abilities. Functional vision is therefore a behavioral consequence of visual function. Changes in functional vision (e.g., vision improvement, correction, rehabilitation, etc.) can be ascertained by objective performance of a controlled task requiring vision. Task performance may be scored based upon timing and error rate. Patient reported outcomes are a measure of changes in daily activities, as reflected, for example, by performance of routine day-to-day tasks requiring vision.

Exemplary implementations disclosed herein provide a test of functional vision measured at varying luminance levels. The test may be designed to evaluate the ability of a subject to navigate a marked path, while avoiding obstacles, relying on vision rather than kinesthetic input. Separate outcome measures may assess visual function and the subject's perspective of his/her ability to perform vision-related tasks.

The test may evaluate whether a subject can detect visual cues (e.g., obstacles, course directionality indicia such as arrows or markers) to navigate successfully and avoid obstacles on a series of obstacle courses. The subject may perform the test using each eye individually, randomized in terms of order, and then with both eyes. Thus, the invention is applicable to evaluating functional vision of either one or both eyes.

Luminance can be altered and varying (e.g., decreasing) levels of luminance used for the test. Luminance levels may be adjusted to the subject's ability, but rounded to a nearest standardized luminance level. In some implementations, between each individual walk-through (or "run"), the course layout may be modified to one of a number of pre-determined course layouts, with the order of courses being determined through randomization prior to a visit to prevent memorization and to reduce the potential for improvement in performance through learning effect.

According to some implementations, individual course layouts may include the same number of arrows, turns, and obstacles. Run through the course may be videotaped using high-definition cameras capable of capturing clear images at low luminance levels. Trained, masked reviewers may score each recording. Speed and/or accuracy may be used in determining whether a subject passes or fails each individual run. The time to complete the course (i.e., speed) may equal a duration starting from a time of an indication to the subject to perform a run to a time of completing the course. The accuracy may be quantified based on a number of collisions (e.g., a forceful body contact with an object). The accuracy may be quantified based on a number of times the subject moved off-course. The subject may be off-course when both of the subject's feet are outside of a boundary of a path through a given course.

According to various implementations, a given subject may have normal vision. In other implementations, a subject may have or be suspected of having vision impairment or deficiency in one or both eyes.

In further implementations, a subject may be a candidate for one or more of ocular therapy or surgery, gene therapy, and/or other ocular treatment. The ocular therapy, surgery, gene therapy, and/or other ocular treatment may be for treatment of Leber's congenital amaurosis (LCA), choroideremia, Retinitis pigmentosa, Stargardt Diesease, Achromatopsia, Congenital stationary night blindness, Usher Syndrome, Bardet-Biedl syndrome, glaucoma, diabetic retinopathy, retinopathy of prematurity, sickle cell disease, ocular albinism, and/or other conditions.

The test may be performed prior to the subject undergoing treatment. In some implementations, the subject has already received one or more of ocular therapy, surgery, gene therapy, and/or other ocular treatment. The test may be performed after the subject underwent one or more of ocular therapy, surgery, gene therapy, and/or other ocular treatment. The test may be repeated over a recovery period to measure improvement or decline associated with one or both of ocular therapy, surgery, gene therapy, and/or other treatment.

Changes from baseline findings may measure the clinical efficacy of an ocular therapy or treatment in that an increase in visually-based orientation and mobility skills increases an individual's safety and independence, and gaining the ability to orient and navigate at reduced duration and/or lower luminance levels than previously possible results in improvement of those activities of daily living that depend on vision. The luminance levels utilized for this testing are routinely encountered in day-to-day situations, such as walking through an office building, crossing a street at dusk, or locating objects in a dimly-lit restaurant. The restoration of any degree of functional vision will have a significant impact on the quality of life for those challenged with visual impairment.

FIG. 1 illustrates an apparatus 100 configured for performing a test of visual function and/or functional vision at varying luminance levels, in accordance with one or more implementations. The apparatus 100 may include one or more courses 102. A given course 102 may comprise a layout 104 having a beginning point 106, at least one turn 108, at least one obstacle 110, an ending point 112, and/or other components. According to some implementations, each of the courses 102 may have different layouts 104. In some implementations, apparatus 100 may include at least one light source 114, at least one camera 116, and/or other components.

The beginning point 106 of a given course 102 may be the position at which a subject begins a run through the given course 102. Examples of beginning point 106 may include one or more of a starting line, a gate, a door, and/or other point or region at which a subject begins navigating course 102.

A turn 108 may be a location within a course 102 at which a subject is to turn while navigating course 102. In some implementations, turn 108 may be marked by a directional arrow. A given course 102 may include any number of turns 108. For example, a course 102 may include a number of turns between one and five, a number of turns between five and ten, a number of turns between ten and fifteen, or a number of turns that is fifteen or more. In some implementations, individual ones of the layouts 104 for different courses 102 may comprise the same number of turns 108. Turns 108 may be of any degree from about 1 degree to about 360 degrees including, for example, about 25 degrees, 30 degrees, 45 degrees, 75, degrees, 90 degrees, 180 degrees, 270 degrees, 360 degrees, or any value in between or fractions thereof. Turns 108 may comprise smooth, gradual turns or sharp turns. Turns 108 may be combined with other features including, without limitation, gradual incline, gradual decline, at least one obstacle 110, textural changes in the surface, such as rough or smooth, and/or one or more changes of direction immediately into other turns 108 of opposite direction.

An obstacle 110 may be anything within a course 102 that a subject is to avoid, circumvent, traverse over, and/or otherwise avert while navigating course 102. According to various implementations, examples of obstacle 110 may include one or more of an object placed adjacent to a path of a given course 102, a raised tile, a tile having a specific color indicative of obstacle, an edge of a step, a change in surface texture, for example from smooth to rough and/or hard to soft. Obstacle 110 may also include inclines, declines, undulations, any of which may vary in degree/grade. Inclines and/or declines may be aligned with axially along the path of a given course 102 or may be disposed at an angle relative to the axial direction of the path of a given course 102. For example, a right or left side of the path may be somewhat higher or lower than the other side such that a person traversing the path would find their right or left side disposed higher or lower than their other side. An obstacle may include a reflective surface representing water or a slippery material.

A given course 102 may include two or more differing obstacles 110. Obstacles 110 may differ in size, shape, type, and/or other manners. A given course 102 may include any number of obstacles 110. For example, a course 102 may include a number of obstacles between one and five, a number of obstacles between five and ten, a number of obstacles between ten and fifteen, or a number of obstacles that is fifteen or more. In some implementations, individual ones of the layouts 104 for different courses 102 may comprise the same number of obstacles 110.

A path through a given course 102 may have a variety of lengths and widths, according to various implementations. For example, a path of a given course 102 that must be navigated to successfully complete the given course 102 may be between ten feet and twenty feet, between twenty feet and fifty feet, between fifty feet and one hundred feet, one hundred feet or more, and/or some other length. A path of a given course 102 may have a width of three feet or less, or three feet or more. A path may include an incline, a decline or a combination of inclines and/or declines of varying grades or degrees (e.g., from 1 to about 30 degrees) or an undulating path with a series of connected inclines and declines. A path may have a smooth or rough surface texture, or a combination of smooth or rough surface texture. A path may have a hard or soft surface or a combination of a hard or soft surface. A path may have a reflective surface representing water or a slippery material.

The ending point 112 of a given course 102 may be the position at which a subject ends a run through the given course 102. Examples of ending point 112 may include one or more of an ending line, a gate, a door, and/or other point or region at which a subject ends navigating course 102.

Individual courses 102 may comprise a grid of tiles or squares. Individual ones of the tiles or squares may be blank or may include a directional indicia, such as an arrow, or an obstacle. FIGS. 2-13 illustrate exemplary course layouts 104, in accordance with various implementations. Each implementation of layout 104 illustrated in FIGS. 2-13 include a beginning point 106, at least one turn 108, at least one obstacle 110, an ending point 112, and/or other components. At least one camera 116 is also portrayed in each of FIGS. 2-13.

According to some implementations, a given layout 104 may be 5 feet by 10 feet with a one-foot border on all edges, with total dimensions being 7 feet by 12 feet. The layout 104 may be printed on heavy white cloth with black arrows and/or other graphics. The layout 104 may have background color of white and/or other colors. Directional arrows may be standardized to dimensions consistent with Snellen lettering for VA of 20/200 in office lighting conditions. Directional arrows used with adults and older children may be sized so that they can be identified with a Snellen 20/200 visual acuity at 2 meters. Allen card figures (e.g., hand) may be used for young children and may be sized so that they can be identified with a Snellen 20/200 visual acuity at 1 to 1.5 meters. Individual subjects may receive follow-up testing using the same type of course 102 (i.e., black arrow or Allen card figure) that they were tested on at the baseline visit. In some implementation of layout 104, black lines may form "tiles." Individual tiles may include a turning arrow, a straight arrow, an obstacle, a black tile representing a hole, a green tile representing grass, a raised tile, a walk-over obstacle, a Styrofoam (or other soft material) object, a stop sign, a trashcan, an ankle-, knee- or waist-high object, and/or other graphics or objects.

Referring again to FIG. 1, a room housing course 102 may be equipped with uniform lighting (e.g., lighting source 114) configured to provide about one lux to at least four hundred lux. Lighting source 114 may be configured to provide a number of luminance levels. A provided luminance level may be rounded to a nearest of a plurality of standardized luminance levels. The plurality of standardized luminance levels may include one or more of 1 lux, 4 lux, 10 lux, 50 lux, 125 lux, 250 lux, 400 lux, and/or other luminance levels. A provided luminance level may be below an estimated lower light sensitivity cutoff (discussed in further detail herein) or above the estimated lower light sensitivity cutoff.

Luminance levels may be measured using a light meter (not depicted). In some implementations, the same model light meter may be used at all test sites. The light meters may have a maximum resolution of 0.1 lux and an error interval of ≤5% (i.e., lux of 1 will have a range of 0.95 to 1.05 lux). Though light meters are generally stable, they may undergo yearly calibration with the manufacturer to ensure proper functioning. Illumination measurements may be taken at each corner and in the center of course 102. Measurements may be taken at ground level as subjects are asked to follow arrows on the ground. According to some implementations, the luminance level readings should be similar (e.g., lux within 20% of the specified luminance level) at the different areas of course 102.

The camera 116 may be configured to capture still images and/or video and/or audio recordings of layout 102 while it is navigated by a subject. In some implementations, camera 116 may include two digital single lens reflex (dSLR) cameras. Both dSLR cameras may be capable of recording HD video at low light intensities, so that both ends of course 102 (start and finish) can be visualized. The dSLR cameras may automatically set the proper white balance and ISO setting for optimal video recording of the subject and course 102. The field of view of camera 116 may include the entire course 102. In some implementations, a video recording by camera 116 may include a sound recording. A video taken from the furthest position to ending point 112 may be used for scoring/analysis, in some implementations. A video taken from another position may be used as a backup video, which may be accessed if there are significant quality problems with the first video.

One or more cutoffs may be established prior to testing and/or during testing. These cutoffs may include one or more of an estimated lower light sensitivity cutoff, a sub-sensitivity cutoff, a supra-sensitivity cutoff, and/or other cutoffs. An estimated lower light sensitivity cutoff may describe the lowest light sensitivity at which a subject can comfortably navigate course 102. A sub-sensitivity cutoff may describe a luminance level below (i.e., dimmer than) the estimated lower light sensitivity cutoff. A supra-sensitivity cutoff may describe an additional luminance level above (i.e., brighter than) the estimated lower light sensitivity cutoff.

In some implementations, a subject may take several practice (coached) walks through a sample course 102, first without any eye patching (but using their prescription corrective lenses, if applicable) and then with one eye patched, using office lighting conditions (250 lux; see also Section 15.0, FIG. 1). A sample course 102 can be a practice run to acclimatize the user to the nature of a typical course, but may not include any actual measurements. A sample course 102 can also include measurements which be used as a baseline run to assist in selecting a follow-on course 102. The subject may also take one or more practice tests with dimmer light. The same sample course 102 may be used for all subjects. The sample course 102 may not be used in actual testing. Practice runs may be recorded. The corresponding video recordings may be retained with subject source documents; however, they may not be submitted for scoring to the independent reviewers.

During this initial practice session, the subjects may be provided with basic instructions and guidance for completing the test. Subjects may be instructed to do their best to avoid all the obstacles and stay on the path. In attempt to discourage young children from hurrying through the test and increasing the likelihood of errors, the test administrators may encourage the subjects to take their time and focus on accuracy. The test administrator may remind the subject not only to look down for the arrows showing the direction to walk, but also to scan back and forth with their eyes so as to avoid obstacles on the ground, or up to eye level. For young children (e.g., ages 3-6 year old), black arrows may be replaced with age-appropriate icons (e.g., a picture of a hand, pointed finger, or the like) of the same color. Subjects should rely on their vision to navigate course 102, as opposed to using their feet and/or hands to feel for objects. Subjects may not use any assistance during the test (e.g., a blind cane, a guide dog, verbal clues, and/or other assistance) but should feel free to verbally identify objects while going through course 102. Subjects may have each eye patched at times.

The test administrator may stop a subject if they are about to trip on an object or otherwise injure themselves. The test administrator may provide no directions while the test is in progress. If the subject asks for directions, the test administrator may tell them to take a guess. However, the test administrator may "re-guide" the subject physically if he/she walks off course 102.

If the test administrator feels that a subject is unable to carry out the test reliably at baseline (e.g., due to age, cognitive ability, and/or other limiting condition), the test administrator may recommend that the subject be excluded from participation in the study.

Baseline testing may provide a calibration of: 1) the light sensitivity at which the individual can navigate (typically, estimated lower light sensitivity cutoff) and 2) a level of light at which the individual cannot navigate (sub-sensitivity cutoff). Prior to dark-adaptation, one eye may be patched and the subject may be shown the practice course 102 in a room with dim light. Dark adaptation may describe a procedure in which light is eliminated or reduced from a subject's view for a designated period of time. This may be accomplished by patching both eyes of a subject and/or by having the subject sit in a darkened or dimly lit room. The test administrator may turn up the light until the subject thinks he/she could just barely carry out the test. This level may be rounded off to one of the standardized luminance levels. This level may be identified as the subject's estimated lower light sensitivity cutoff for the given eye. This process may then be repeated with the other eye patched. During this process, the subject may be allowed to walk around or on the practice course 102. If the subject cannot carry out the test at the estimated lower light sensitivity cutoff described above, an additional luminance one specified luminance level above the estimated lower light sensitivity cutoff (supra-sensitivity) may be used. If, at baseline, the subject overestimates his/her estimated lower-light sensitivity cutoff and is able to pass course 102 at the sub-sensitivity cutoff, this luminance level may be identified as the estimated lower light sensitivity cutoff and testing will proceed to a lower specified luminance level at which the subject is unable to navigate course 102. This level may be documented as the subject's sub-sensitivity cutoff.

Test administrators may determine luminance levels for follow-up visits based on their assessments of a subject's performance at the prior study visit. The decision may not require feedback from the independent reviewers scoring the test. At follow-up visits, test administrators may attempt to identify a luminance level at which the subject can pass course 102 and one at which the subject cannot pass course 102. In this way, test administrators can capture improvement as well as degeneration of subjects. If the subject appears to navigate accurately at a given specified luminance level, the next visit's testing may occur at 1) this same luminance level and/or 2) one step lower on the specified light scale. If the subject appears to have difficulty navigating accurately at a given specified luminance level, the luminance level may be maintained or increased at the subsequent follow-up visit. For example, if a subject who could not navigate at 125 lux at baseline successfully navigates at 125 lux during his/her initial follow-up visit, testing may occur at the next lower level during the subsequent visit (50 and 125 lux). If the subject successfully navigates at 50 lux at this visit, he/she would be tested at a lower specified luminance level at the next visit (10 and 50 lux), but if the subject has difficulty navigating, he/she may be tested again at 50 and 125 lux. Conversely, if the subject passes at 125 lux during his/her initial follow-up visit but fails at 125 lux at his/her subsequent visit, the test administrator may continue to test at higher luminance levels (250 and/or 400 lux) in order to identify a level at which the subject can pass the test.

According to some implementations, a given layout 104 may be standardized for number of obstacles, number of turns, size of arrows, type of obstacles, and/or other features or components. In some implementations, there may be a total of twelve different configurations in use (in addition to the sample course 102). The path for the subject to follow may be indicated with standardized colored (e.g., black) arrows on a contrasting (e.g., white) background. The layout 104 may be changed prior to each run. The order of layouts 104 used may be randomized prior to each subject visit. The test may be carried out in a room that has uniform lighting capable of illumination of 1 to 400 lux and which is controlled by a "dimmer" switch. Testing may begin at the subject's pre-determined luminance level. By way of non-limiting example, luminance levels typically experienced by an individual over course 102 of a day may include 400-450 lux used in dental/surgical procedures, photography, and to facilitate certain manual procedures (for example, jewelry making or watch repair); 250 lux used by most office/laboratory workers carry out their tasks; 125 lux used for lighting in gathering spots (such as lobbies and terminals); 50 lux used for stairwell lighting; 10 lux provided by typical streetlights for vehicles on roads; 4-5 lux encountered by an individual walking on an unlit sidewalk at night; and 1 lux in the middle of a moonless summer night.

The subject may be dark-adapted for a period of time while course 102 is configured for the actual testing. The duration of dark-adapting may be from 10 to 60 (e.g., from 20 to 40) minutes, or some other duration. During dark adaptation, the subject may perform another test that is compatible with the level of light (e.g., providing verbal responses to a questionnaire).

Following dark-adaptation, the test administrator may guide the subject to beginning point 106 the first randomly selected course 102. Individual runs may begin when the test administrator provides an indication such as saying "Go" or "Start" (or the equivalent in another language). Individual runs may end when the subject reaches ending point 112. In some implementations, the end of a run may be established once a subject touches an object (e.g., a doorknob) at ending point 112, or the test administrator indicates that the test is over.

Once the subject completes the first run, layout 104 will be changed (with the subject out of the room or in the room with both eyes patched). The subject may traverse course 102 again, but with a different layout 104, with the opposite eye patched. Tests may be carried out using each eye alone (through patching) and/or with both eyes open at estimated lower light sensitivity cutoff and sub-sensitivity cutoff levels. If the baseline estimated light sensitivity cutoff differs significantly from one eye to the other, additional tests may be performed. In some implementations, the sub-sensitivity cutoff testing may be carried out first, followed by testing at the estimated lower light sensitivity cutoff and then, finally (if warranted at baseline), by testing at supra-sensitivity cutoff levels.

If the subject goes off course and does not correct him/herself after a number of steps (e.g., 2, 3, or more), or if the subject is about to bump into an object or risk injury, the test administrator may guide the subject back onto course 102. When re-guiding a subject, the test administrator may give a verbal cue to aid in video scoring and adjudicating. If the subject does not know which way to go and pauses for more than 15 seconds, the test administrator may recommend that the subject choose a direction, assuring the subject that the test administrator will stop him/her if that particular direction puts the subject at risk of getting hurt.

According to some implementations, a subject may take a plurality of tests, e.g., two, three, four, five or more, such as six different tests at each visit. These may be carried out at the two levels of luminance (sub-sensitivity and estimated lower light sensitivity cutoff levels, conducted successively) and with the right and left eye patched individually and then with neither patched. Those individuals who have an estimated lower light sensitivity cutoff greater than 250 lux may have testing carried out at 250 lux and 400 lux (still providing six tests) although obtaining a "supra-sensitivity cutoff luminance" may not be possible. An additional (supra-sensitivity) luminance may be used for two or three more tests (at baseline) if the subject cannot carry out the test at the "estimated lower light sensitivity cutoff." If it is not possible to complete all testing in a single day, additional tests may be carried out on a subsequent day. If two days of testing are to be used, testing at the lowest light intensities may be carried out on the first day of testing. If the baseline estimated light sensitivity cutoff differs significantly from one eye to the other, there may be additional tests beyond six tests. In that situation, there may be a total of up to twelve different tests. In such a scenario, testing may be split between two days beginning with the lowest light intensities and proceeding to the higher.

In accordance with some implementations, trained readers, who may be independent of the study and masked to participants' treatment group (if applicable), may carry out scoring. An additional individual may be trained as an adjudicator. The readers and adjudicator may have been trained as a group before testing begins. The trainer may describe the test and scoring rules, and may show videos to demonstrate the scoring approach. The trainer may provide the readers and the adjudicator with one set training videos. The readers and adjudicator may review and score the videos in the set together. The trainer may then meet with the readers and adjudicator to review the procedures and answer any questions. The readers may then review a second set of videos independently and meet with the adjudicator to compare their final scores. The independent review process and comparison of scores may be repeated until the two readers and adjudicator feel comfortable with the process and agree on their final scores. Training may be complete when the trainer is confident in the readers' ability to score the videos accurately. If additional readers are needed after the study has initiated, the training process for new readers will be repeated with the group as described above.

In some implementations, individual test videos may have numeric or alphabetic labels assigned randomly according to subject, visit number, date, eye patching, and/or other information. Those numeric or alphabetic labels may be embedded at the start of individual videos. Two trained readers may grade individual labeled videos independently. The readers and adjudicator may not be provided with any subject information including the subject's alphanumeric identifier, date, subject visit, luminance level of the test, whether or not an eye is patched, and/or other subject information. If a soundtrack of the test is available, it may be on when the video is being graded. A sound recording device may be part of a video device or may be a separate device apart from the video device. This may provide useful additional information in case the video image is not clear (e.g., the sound of a "bump" or comments from the subject or test administrator). The files may be viewed with Windows™ Real Player™ software, Apple™ Quicktime™, and/or other video viewing software or equipment. The videos may be viewed in "full screen" mode and sound may be on. Audio speakers may be available during grading. The brightness and/or contrast may be modified in order to clarify the events on the video. In some instances, it may be helpful to review the videos (or portions thereof) multiple times in order to get an accurate score.

Two trained readers may watch the video and determine the number of collisions and/or the time to navigate course 102. They may record the number of times that the subject goes off course, the number of tiles that are bypassed, and/or the number of times that the subject is re-directed. The number of collisions with obstacles and other errors (e.g., going off course) may be used during data entry to assign penalties for both speed and accuracy. In some implementations, the accuracy score may be a sum of collisions and accuracy penalties. The time score may be determined by combining the seconds to complete course 102 with time penalties. A "pass" or "fail" indication may be assigned separately for both accuracy and speed.

The reader may record each collision with an obstacle. A collision may be described as forceful body contact with any object (e.g., kicking an object, stepping directly and/or forcefully into an object). The readers may record every obstacle that is bumped as a collision. The same obstacle bumped more than once may be considered only one collision. Every obstacle that is kicked in order to feel it may be recorded as a collision. Every obstacle that is bumped with out-stretched hands or arms may be recorded as a collision. In some implementations, it may not be considered a collision when a subject picks up an obstacle (i.e., can see where it is to be able to grasp it). A collision may not be designated if the subject tries to step over an obstacle jutting in his/her way but bumps it in the process. If the subject brushes against an obstacle while progressing along the path delineated by the arrows (even if the object moves slightly), this may not be designated as a collision.

A subject who has both feet off of the path may be considered as being "off course." In some implementations, being off of the path may mean having both feet on tile(s) that do not have arrows. If a subject's foot straddles the border of an adjacent tile, this may not be considered "off course." The reader may record every instance that a subject initiates an off-course event. After placing both feet off the path, if the subject continues to walk off course, this is considered only one off-course event. Collisions while the subject is off course may be counted unless the subject has already bumped into a given obstacle. It may not be considered an off-course event if the subject steps backward on course 102 to take a second look. However, if an obstacle is bumped, this may be noted as a collision. Leaning over to get a closer look may not be considered an off-course event. If the subject finds his/her way back to course 102, no further penalties may be assigned.

If a subject steps off course (has both feet outside the path) and needs assistance from the test administrator to find his/her way back onto the path, this may be considered re-guiding. To aid in scoring, the test administrator may provide a verbal cue when a subject is re-guided. The readers may indicate how many times the subject was re-guided.

The subject may be penalized for bypassing or skipping portions of the course. For example, in some implementations, if the subject bypasses tiles with arrows on course 102, the subject may be penalized. The readers may indicate the number of tiles (with arrows) that are bypassed.

Time to complete course 102 (i.e., speed) may be measured from the point in time when the test administrator provides an indication to the subject to perform a run of the test until then point in time when the subject reaches the ending point 112 (or the test administrator indicates the run is over). The readers may record the time (e.g., minutes/seconds) indicated on the video at the start and at the stop of the run. If the subject does not complete course 102, the reader may record the start time and stop time (as indicated by the subject or test administrator). In such a case, the reader may indicate that the subject was unable to complete course 102. If the subject does not complete course 102, an arbitrary time (e.g., 4 minutes, 30 seconds) may be assigned during data entry. This assignment may be useful for subjects who hesitate to move in any direction.

The two readers each may complete a form or questionnaire after watching individual videos. In some implementations, the readers may select a descriptor indicating the quality of the video with respect to grading purposes. The readers may enter data in all the designated spots on the form or questionnaire. The entered data may include one or more of times at which the subject starts and finishes navigating course 102, whether the subject was able to complete course 102, number of collisions, number of times off-course, number of times re-guided, number of tiles bypassed, comments made by the subject, number of kicks or hand movements or other signs that the subject is unsure of the location of the obstacles and/or other information. The readers may record their initials and the date on which the test was graded.

At regular intervals, the readers may meet to openly adjudicate the videos and aim to reach a consensus. If the readers cannot agree on something during this process, the adjudicator may review the videos with them so that consensus may be reached. The adjudicator's decision may be final, in some implementations. If one or both of the readers has indicated that the overall video is not evaluable because of a significant recording issue, the adjudicator may request the back-up video be provided for grading. In this circumstance, the back-up recording may serve as the final scored recording.

A data entry technician may enter data obtained during grading into a database. The database may generate reports. Examples of such reports may include ones for case record form (CRF) completion, quality assurance, inter-grader variability, and/or other reports. During data entry, penalties may be assigned for both accuracy and speed. In some implementations, penalties may be weighted to make accuracy more important for passing the test. This weighting may be intentional because personality may influence how quickly a subject completes course 102.

Penalties for accuracy may arise from a number of different situations. Each collision with an obstacle may result in an accuracy penalty of one point. Stepping off course 102 may result in an accuracy penalty of one point for each off-course event. If the subject is re-directed by the test administrator, each re-direction event may be assigned one accuracy penalty point. A subject who bypasses tile(s) may receive an accuracy penalty of one point for each tile on the path that is bypassed. Accuracy penalties for bypassing tiles may or may not coincide with penalties for going off course. For example, if a subject steps off course and then bypasses several tiles before returning to course 102, one point may be assigned for going off course and one point for each tile bypassed. If a subject bypasses a tile without stepping off course, there may not be a point assigned for going off course but one point may be assigned for each tile bypassed. The subject may receive more accuracy penalty points than there are obstacles. A perfect accuracy score is "zero," according to some implementations Penalties for speed may arise from a number of different situations. If the subject is redirected, there may be a time penalty (e.g., 30 seconds) that is assigned. In addition to an accuracy penalty, a 15 second penalty may be assigned for each tile that is bypassed and/or for each time the subject is completely off course 102.

The scores for accuracy and speed may be calculated using an algorithm as an "accuracy score" and a "time score." A "pass" or "fail" indication may be designated for each. In some implementations, a pass for accuracy may require an accuracy/penalty score of ≤0.25 (at least 75% accurate). This score may be determined based on collisions and other accuracy penalties compared to the total number of obstacles. A pass for time may require a time score of less than 3 minutes, according to some implementations. This determination may include the time the subject takes to complete course 102 as well as any time penalties. If there is a pass indication for both accuracy and speed, the final Score may be "pass." If there is a fail indication for either accuracy or speed, the final score may be "Fail."

If the readers have indicated that they are unable to grade collisions with 3 or more obstacles, the data entry specialists may indicate that a Pass or Fail designation could not be made for accuracy ("NA"). The final score may be NA unless the subject has failed on the basis of time. For example, if the technicians cannot see a section of course 102 clearly, but it is apparent that the subject could not find ending point 112 within 3 minutes, the subject may fail on the basis of time and the final score is fail.

Figure 14:
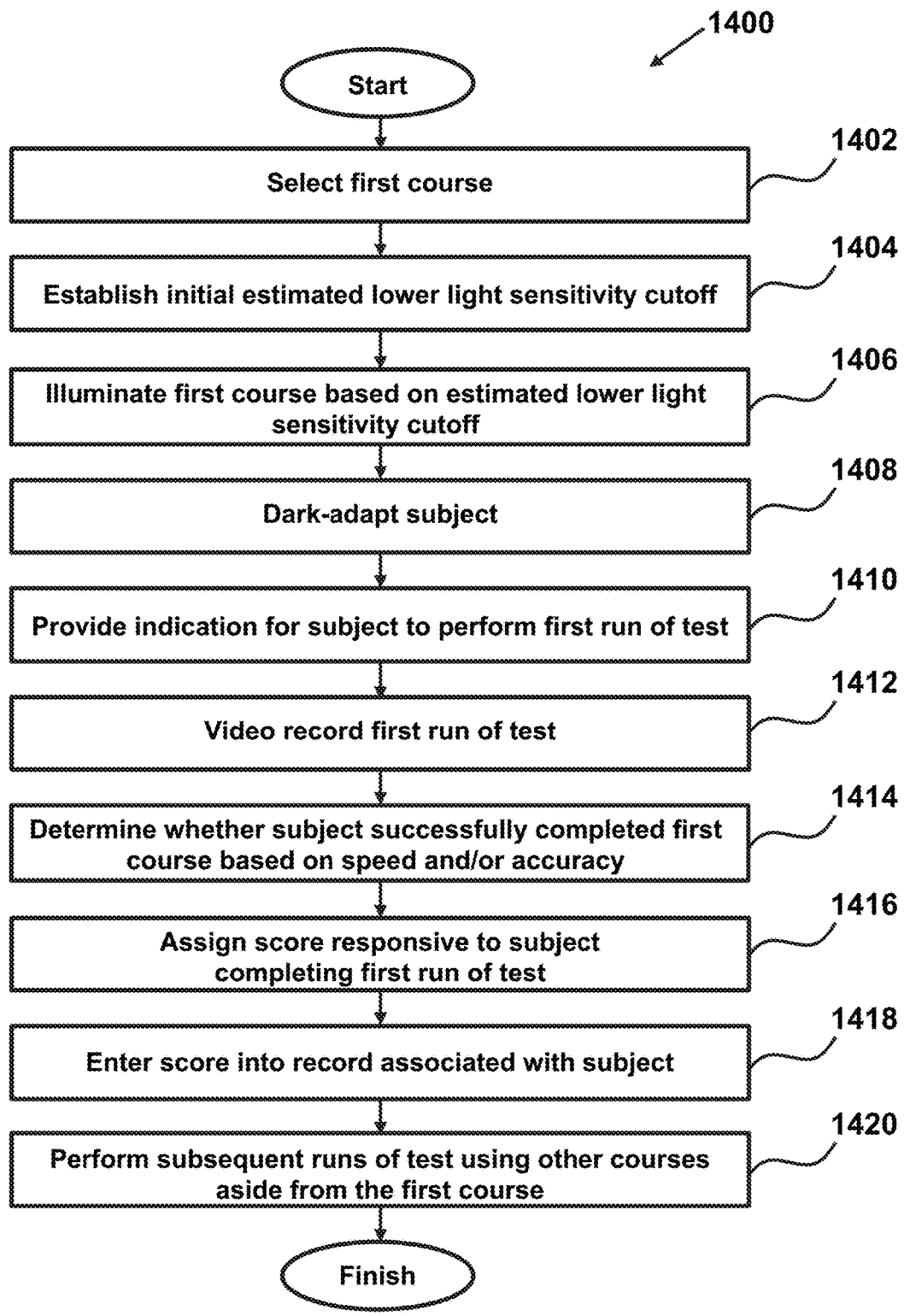
FIG. 14 illustrates a method for performing a test of visual function and/or functional vision at varying luminance levels, in accordance with one or more implementations.

FIG. 14 illustrates a method 1400 for performing a test of visual function and/or functional vision at varying luminance levels, in accordance with one or more implementations. The steps of method 1400 presented below are intended to be illustrative. In some implementations, method 1400 may be accomplished with one or more additional steps not described, and/or without one or more of the steps discussed. Additionally, the order in which the steps of method 1400 are illustrated in FIG. 1400 and described below is not intended to be limiting.

At a step 1402, a first course (e.g., course 102) of a plurality of courses may be selected for a subject. A given one of the plurality of courses may comprise a layout having a beginning point, at least one turn, at least one obstacle, and an ending point.

At a step 1404, an initial estimated lower light sensitivity cutoff may be established for the subject. The estimated lower light sensitivity cutoff may be the lowest light sensitivity at which the subject can successfully navigate a preliminary course of the plurality of courses when the estimated lower light sensitivity cutoff is measured.

At a step 1406, the first course may be illuminated with a first luminance level based on an estimated lower light sensitivity cutoff. The course may be illuminated using lighting source 114.

At a step 1408, the subject may be dark-adapted by prohibiting light to reach the subject's eyes for about thirty minutes to forty minutes.

At a step 1410, an indication may be provided for the subject to perform a first run of the test. The test may comprise, from the beginning point to the ending point, navigating the layout of the first course by walking around the at least one turn and avoiding the at least one obstacle.

At a step 1412, the first run of the test may be video recorded using one or more cameras (e.g., camera 116) configured to capture video footage at the first luminance level.

At a step 1414, a determination may be made as to whether the subject successfully completed the first course based on one or both of speed or accuracy. Speed may describe the time to complete the first course. Accuracy may describe avoidance of obstacles and/or no off-course re-guidance or bypassing or skipping portions of the path.

At a step 1416, a score may be assigned responsive to the subject completing the first run of the test. The score may be determined based on one or more of a number of collisions, a number of off-course events, a number of corrections provided by a test administrator, accuracy, or speed.

At a step 1418, the score may be entered into a record associated with the subject.

At a step 1420, subsequent runs of the test may be performed using other corresponding ones of the plurality of courses aside from the first course.

A mobility test validation study ("MTVS" or "study") for visually impaired and normal-sighted subjects has been performed, in accordance with one or more implementations described herein. The study aimed to enroll 30 normal-sighted and 30 visually-impaired individuals. At that time, 62 subjects were enrolled and had signed consent. Of these enrolled subjects, 54 individuals (26 normal-sighted and 28 visually-impaired) were still on study at the time of the data cut-off. Three (3) normal-sighted and 3 visually-impaired individuals discontinued the study early; one (1) of these visually-impaired subjects completed an early termination visit. Two (2) individuals, who are not reflected in the 60 subjects summarized in this report, were withdrawn at screening, as they did not meet protocol-specified eligibility criteria.

The primary focus of the study was to assess the validity of an exemplary implementation of the mobility test ("MT" or "test"). Both visually-impaired and normal-sighted individuals had MT assessments at baseline (twice) and at a one-year follow-up visit. Secondary outcomes included visual acuity, visual fields (Goldmann and Humphrey), and quality of life questionnaire (QOL).

The goals of the study were for the mobility test to construct validity, be reliable, have content validity, and be able to detect change. With respect to construct validity, the test and scoring method were to be able to distinguish those with normal vision from those with impaired vision. For those with impaired vision, the test was to distinguish higher from lower performers. With respect to reliability, the test was to show high inter-observer, test-retest, and intra-observer reproducibility. With respect to content validity, the test was to directly represent aspects of visual fields (VF), visual acuity (VA), and quality of life using the test components of speed, accuracy, score, and improvement score. With respect to ability to detect change, the test was to identify differences in scores over time in subjects whose visual function changed over the period of the study. Conversely, those whose visual function did not change during the period of the study were not to have different MT scores.

Study visits consisted of the following: (1) a screening visit which included consenting/assenting subject and caregiver and inclusion/exclusion criteria screen; (2) two baseline visits which each included a mobility test, a visual fields test, a visual acuity test, and a QOL questionnaire; (3) a follow-up visit at Year 1 which included a mobility test, a visual fields test, a visual acuity test, and a QOL questionnaire.

Sixty (60) consented individuals were enrolled in the study and have baseline data. This includes the 6 subjects who discontinued the study early. Forty-five individuals have Year 1 data. Of these, 25 are normal-sighted, and 20 are visually-impaired. One visually-impaired subject discontinued the study prior to Year 1.

The study provided secondary outcomes of visual acuity, Goldmann and Humphrey visual fields, and quality of life questionnaire scores in relationship to the mobility test components of accuracy score and time. All plots presented in connection with the study include all available data in the database. These include mobility tests at different lux (light) levels and multiple baseline visits for a person. Each data point on a plot represents an individual person's measurement at a visit. The data point itself denotes the person's age at baseline. Mobility test results presented are consensus scores only (not individual graders), though separate Reading Center QA reports have shown there is strong agreement between graders. Change scores are calculated for subjects with available Year 1 or termination visit data.

According to the study, the mobility test and scoring method is able to distinguish those with normal from those with impaired vision; the components of the mobility test (such as time and accuracy score) clearly show this construct validity between those with normal and impaired vision. For those with impaired vision, the test distinguishes higher from lower performers; those with impaired vision show a range of performance. Scoring of the testing shows high inter-observer, test-retest, and intra-observer reproducibility, thereby demonstrating reliability. The test and test components represent aspects of visual field, visual acuity, and quality of life. Preliminary data on the effect for visual acuity and visual field appears to have a cut-off effect, rather than a monotone relationship. Mobility test change scores have been calculated for 46 subjects, specifically 45 subjects who completed a Year 1 visit prior to the data cut-off and an additional subject that completed an early termination visit.

For the bilateral (both eyes) testing condition only, where a change score of 1 (i.e., one specified light level) is considered clinically meaningful: 41/46 subjects had a change score of zero, including all normal-sighted subjects; 5/46 had clinically meaningful negative change scores of −1 or −2, all of which were visually-impaired subjects known or thought to have inherited retinal degenerative disorders; and no subjects analyzed to date have a positive, clinically meaningful change score over the course of one year.

For the sum of R+L+B (all eye-patching scenarios) condition, where a change score of 3 (i.e., one specified light level) is considered clinically meaningful: 38/46 subjects had a change score of zero, including all normal-sighted subjects; 5/46 visually-impaired subjects had slightly negative change scores of −1 or −2; 2/46 visually-impaired subjects had a clinically meaningful negative change score of −3; and no subjects analyzed to date have a positive, clinically meaningful change score over the course of one year, though one visually impaired subject, under the age of 10, had a slightly positive change score of +1 (right eye testing only) from Baseline to Year 1.

For all videos graded, inter-grader agreement between two separate graders was assessed (with 95% confidence intervals) by intra-class correlations for mobility testing components (such as number of obstacles hit and times off-course) and by kappa statistics for course completed, accuracy and time pass/fail, and final pass/fail; percent agreement is also presented for these outcomes. Additionally, every three months a 10% sample of videos from the prior quarter was randomly selected to be re-graded, with a two-fold greater probability of selection for those videos in which collisions and/or penalties have been observed on grading. These videos were mixed with new videos provided to the graders, and graders were not informed that quality assurance was occurring or which videos were new.

Figure 15A:
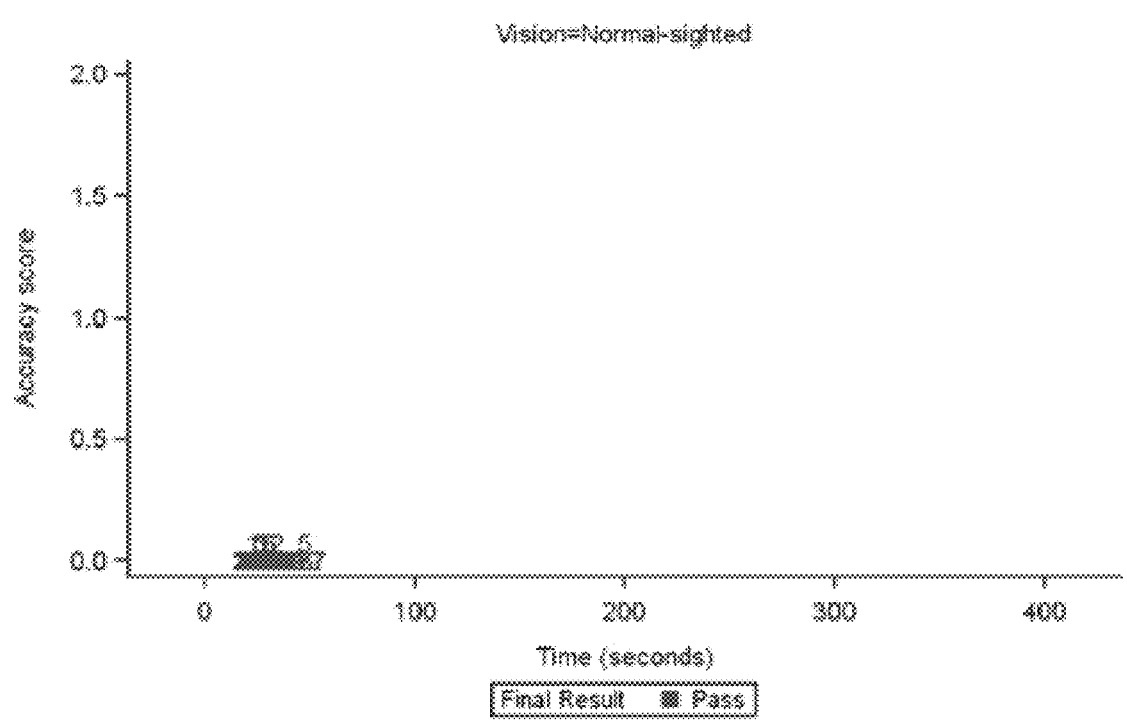
FIGS. 15A and 15B show data obtained during a mobility test validation study for time versus accuracy score, by pass/fail status, for normal-sighted and visually-impaired subjects, respectively.
Figure 15B:
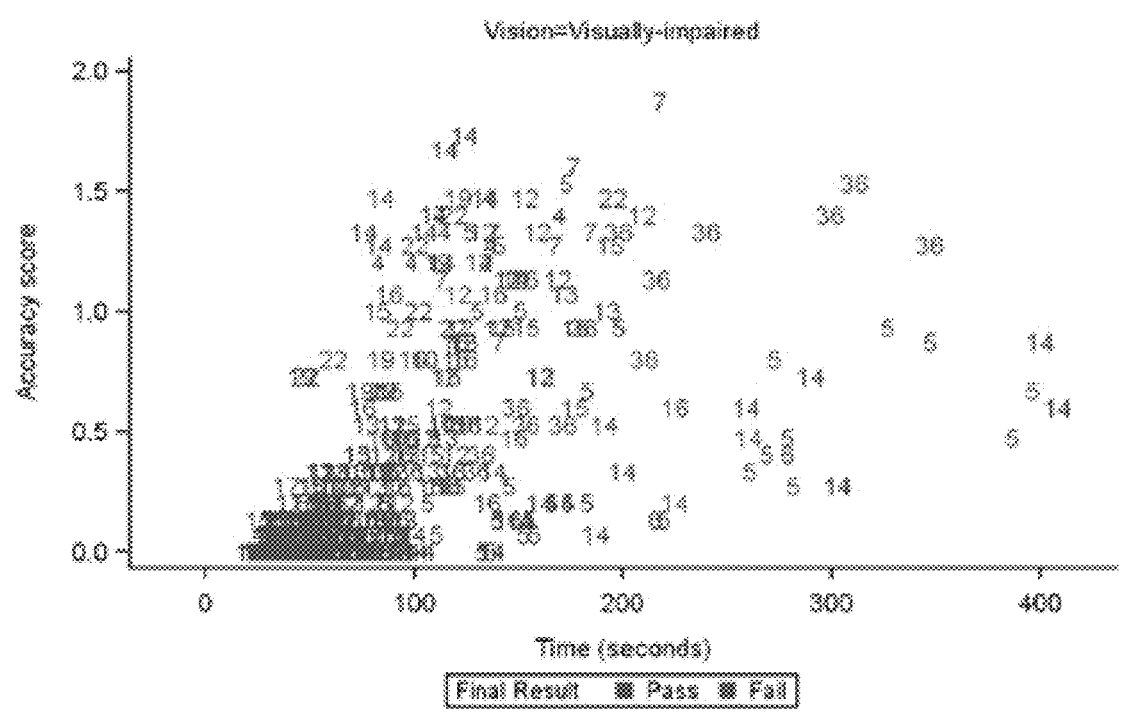

FIGS. 15A and 15B show data obtained during the mobility test validation study for time versus accuracy score, by pass/fail status, for normal-sighted and visually-impaired subjects, respectively.

Figure 16:
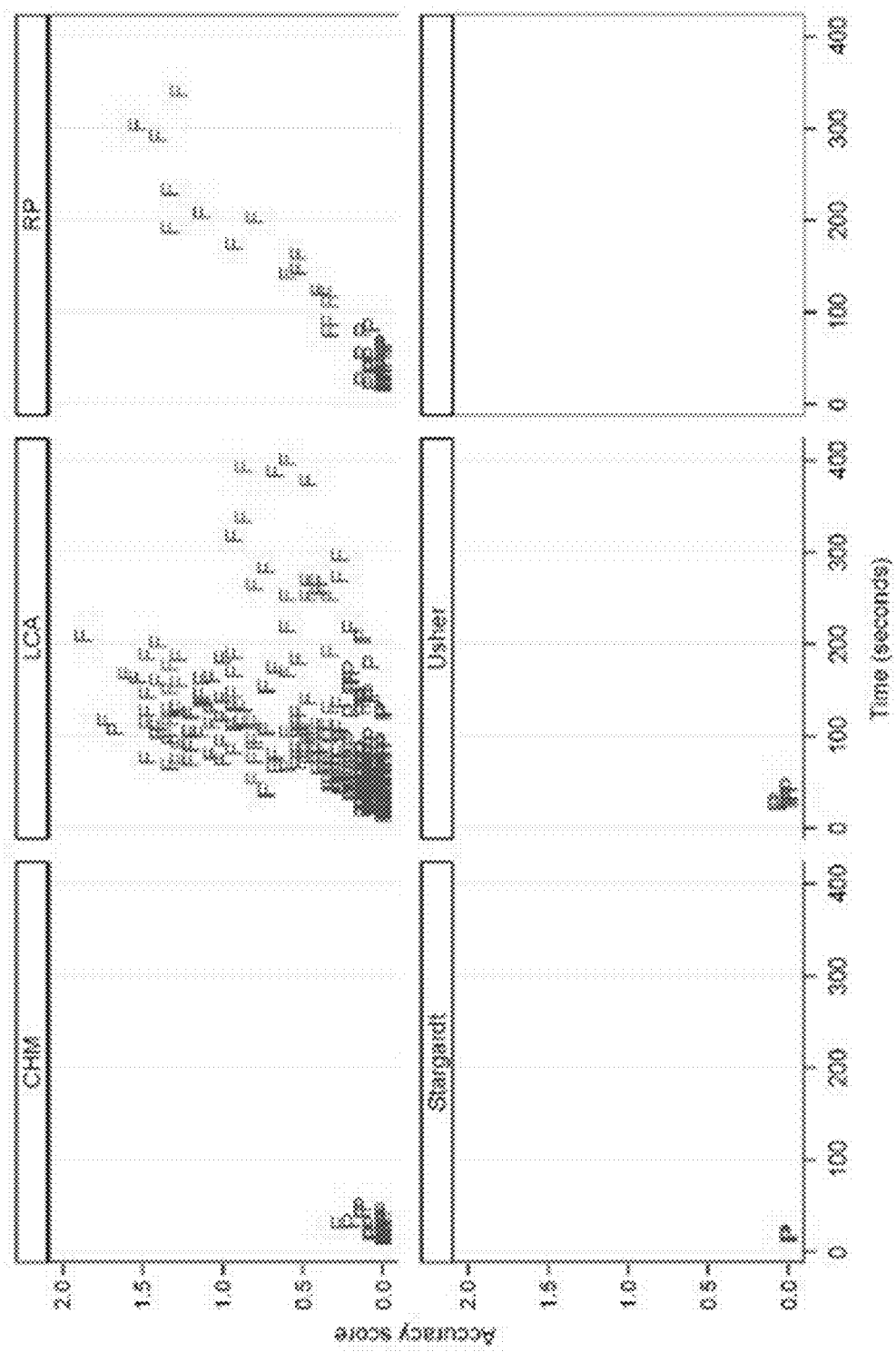
FIG. 16 shows data obtained during the mobility test validation study for time versus accuracy score, by pass/fail light status and clinical diagnosis subset.

FIG. 16 shows data obtained during the mobility test validation study for time versus accuracy score, by pass/fail light status and clinical diagnosis subset.

In the study, visual acuity, Goldmann and Humphrey visual fields, and quality of life as assessed by the visual function questionnaire were compared against the mobility test components of time and accuracy, the primary pass/fail determinant. Penalties were weighted to make accuracy more important than speed; however, if there was a Fail on either accuracy or time scores, the final MT run score was "Fail."

In FIGS. 15-24, each observation in a plot represents a single eye for a person at a timepoint and light level. The metric for visual acuity is calculated as the average of any LogMAR transformed scores (4M, 2M, and 0.5M) at a timepoint, light level, and eye. The exceptions are four visually-impaired subjects who were unable to detect any optotypes. Each observation is numbered with the age of the subject. For plots by person, a color represents observations from the same individual. Because visual acuity and visual field were assessed on individual eyes, FIGS. 17-22 show corresponding mobility test results for individual eyes. These plots exclude mobility tests for both eyes. FIGS. 23 and 24 contain mobility tests results for all three eye-patching conditions. The plots clearly distinguish normal-sighted from visually-impaired subjects. For the impaired subjects, the plot does not necessarily indicate a linear correlation between visual acuity and accuracy score. However, there appears to be a cutoff beyond which the accuracy scores are much greater than zero. A similar phenomenon occurs with time. In both plots, the cutoff for visually-impaired subjects is approximately 0.5 LogMAR units (or 20/63 Snellen fraction).

Figure 17A:
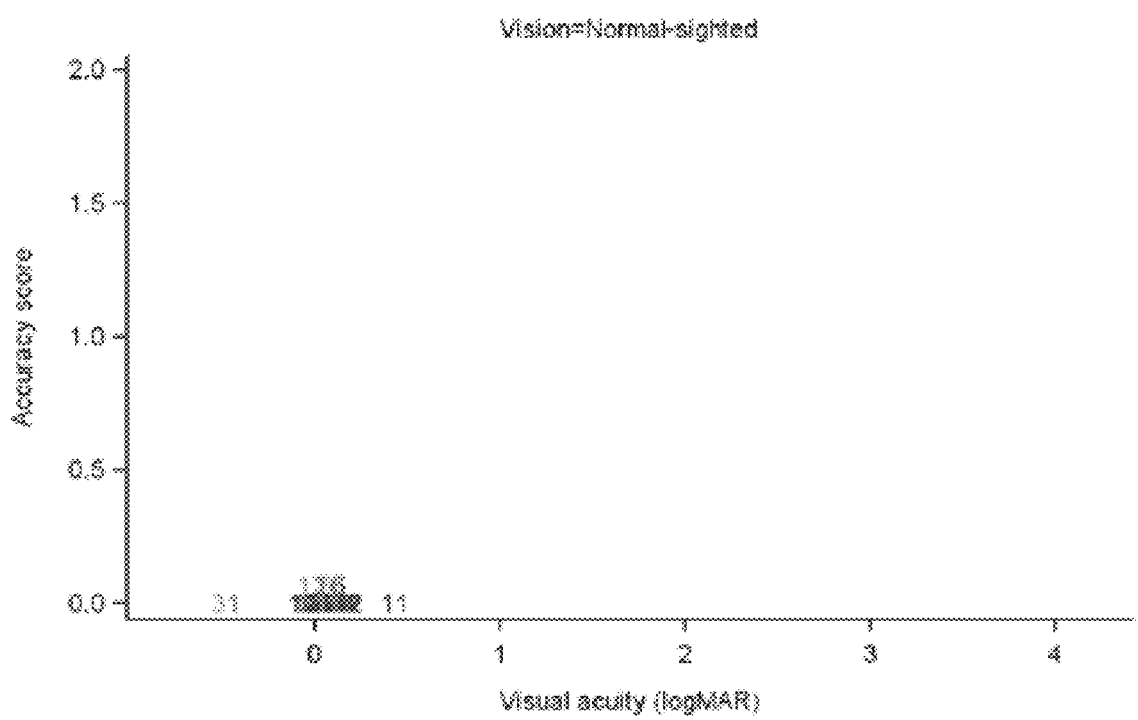
FIGS. 17A and 17B show data obtained during the mobility test validation study for visual acuity versus accuracy score, by person, for normal-sighted and visually-impaired subjects, respectively.
Figure 17B:
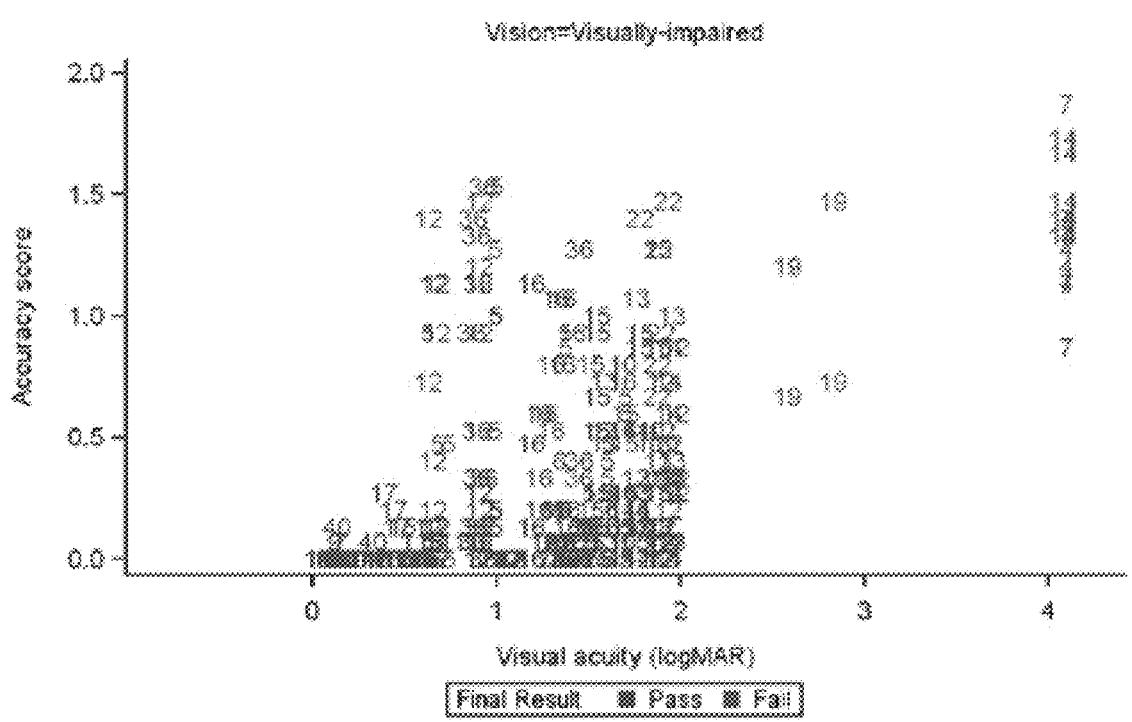

FIGS. 17A and 17B show data obtained during the mobility test validation study for visual acuity versus accuracy score, by person, for normal-sighted and visually-impaired subjects, respectively.

Figure 18A:
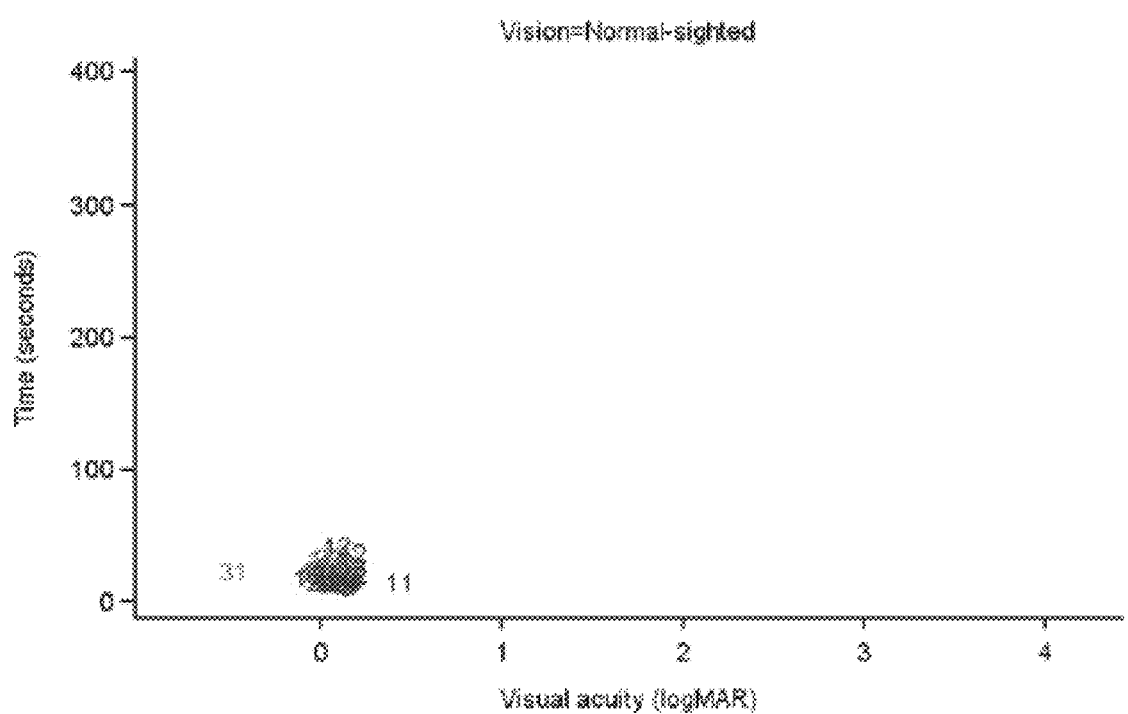
FIGS. 18A and 18B show data obtained during the mobility test validation study for visual acuity versus time, by person, for normal-sighted and visually-impaired subjects, respectively.
Figure 18B:
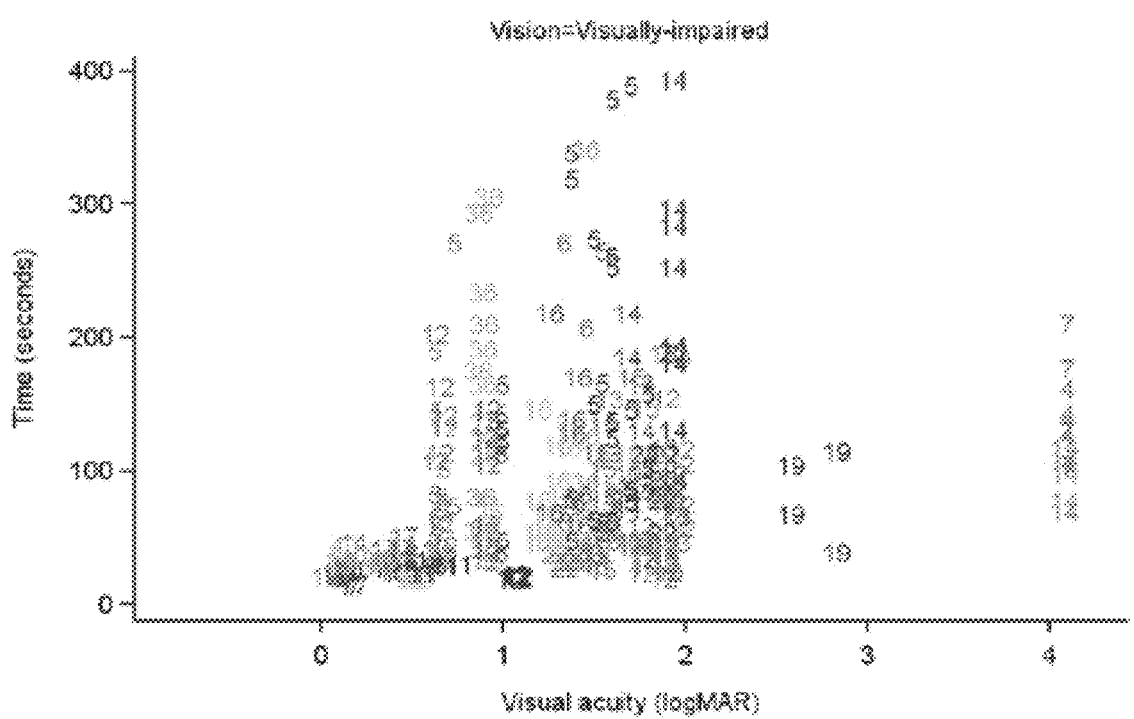

FIGS. 18A and 18B show data obtained during the mobility test validation study for visual acuity versus time, by person, for normal-sighted and visually-impaired subjects, respectively.

For Goldmann visual fields (V4e and III4e), the outcome measure was the sum total degrees; higher sum areas indicate more functional vision. Visual field results from individual eyes were plotted against mobility test consensus scores from the right and left eyes. The plots did not necessarily indicate correlation between visual fields and accuracy score or time. Instead, there appeared to be a cutoff beyond which the accuracy scores are closer to zero (i.e., no errors) occurring around 1000 sum total degrees. The plots suggest a negative correlation between time and visual fields. The cutoff phenomenon also still applies to Humphrey visual fields (foveal sensitivity and macula threshold), with cutoffs among the visually-impaired occurring around 30 dB.

Figure 19A:
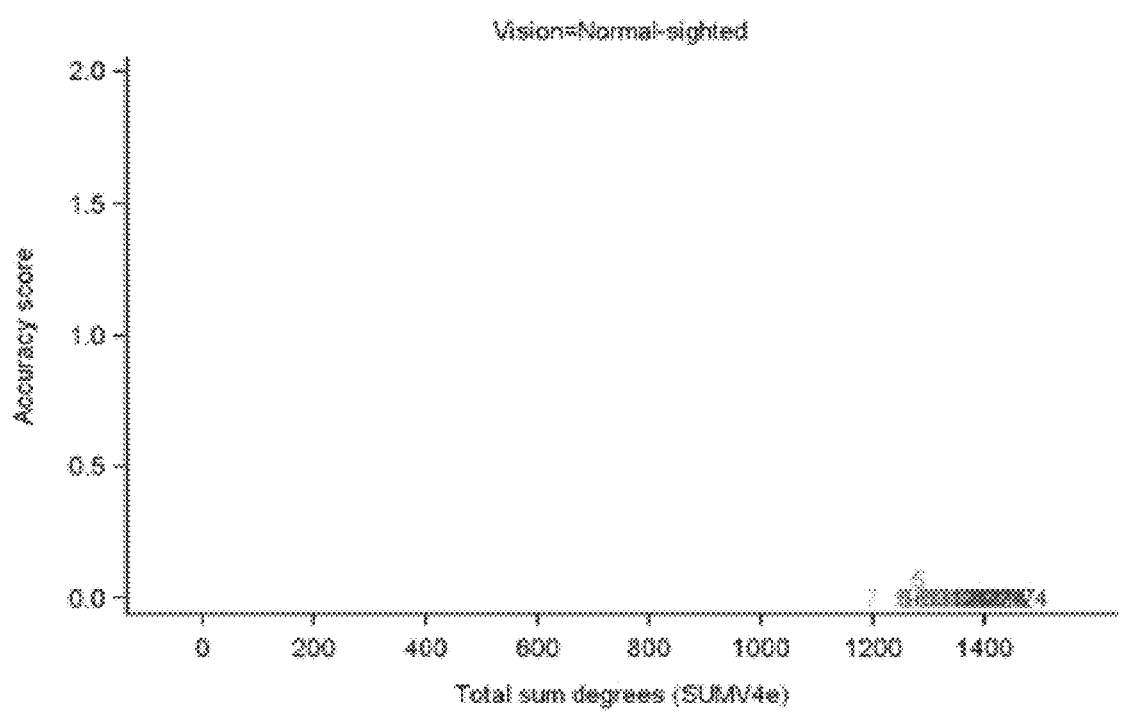
FIGS. 19A and 19B show data obtained during the mobility test validation study for Goldman visual fields (total sum degrees) versus accuracy score, by person, for normal-sighted and visually-impaired subjects, respectively.
Figure 19B:
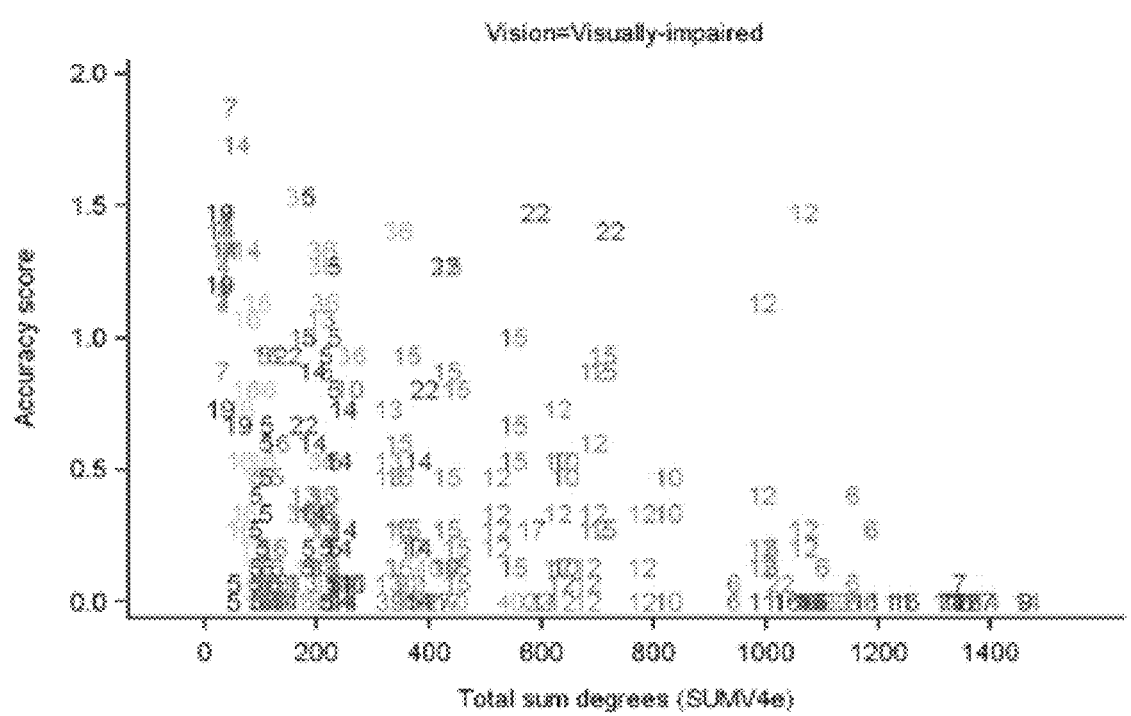

FIGS. 19A and 19B show data obtained during the mobility test validation study for Goldman visual fields (total sum degrees) versus accuracy score, by person, for normal-sighted and visually-impaired subjects, respectively.

Figure 20A:
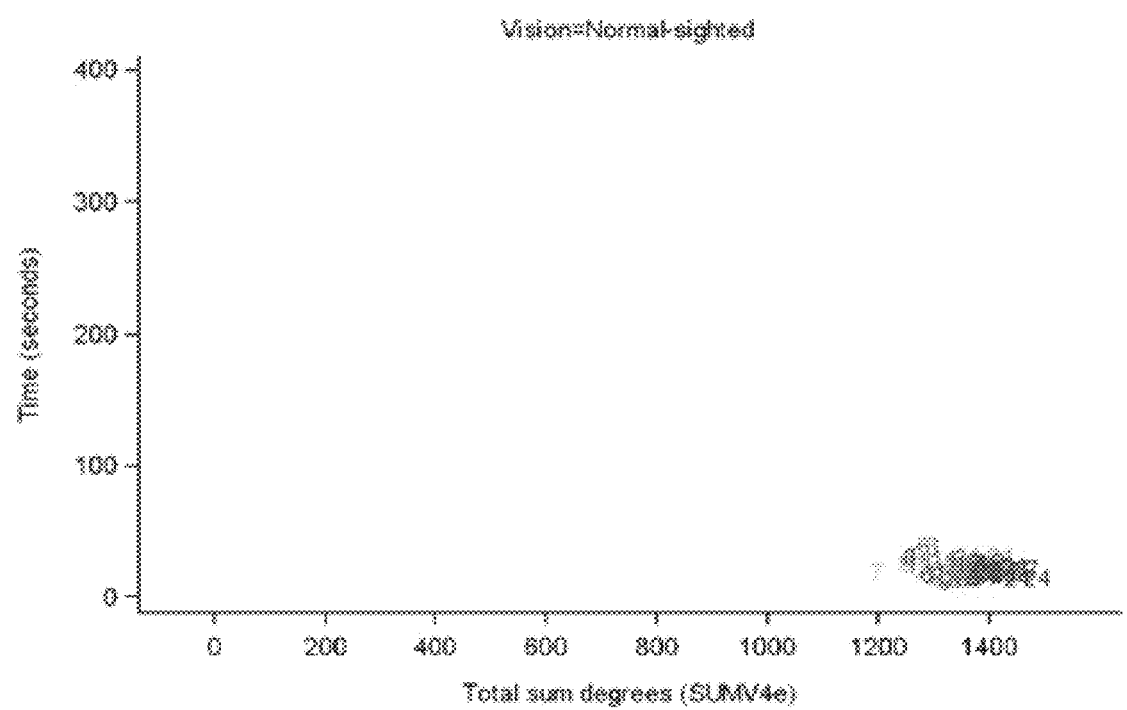
FIGS. 20A and 20B show data obtained during the mobility test validation study for Goldman visual fields (total sum degrees) versus time, by person, for normal-sighted and visually-impaired subjects, respectively.
Figure 20B:
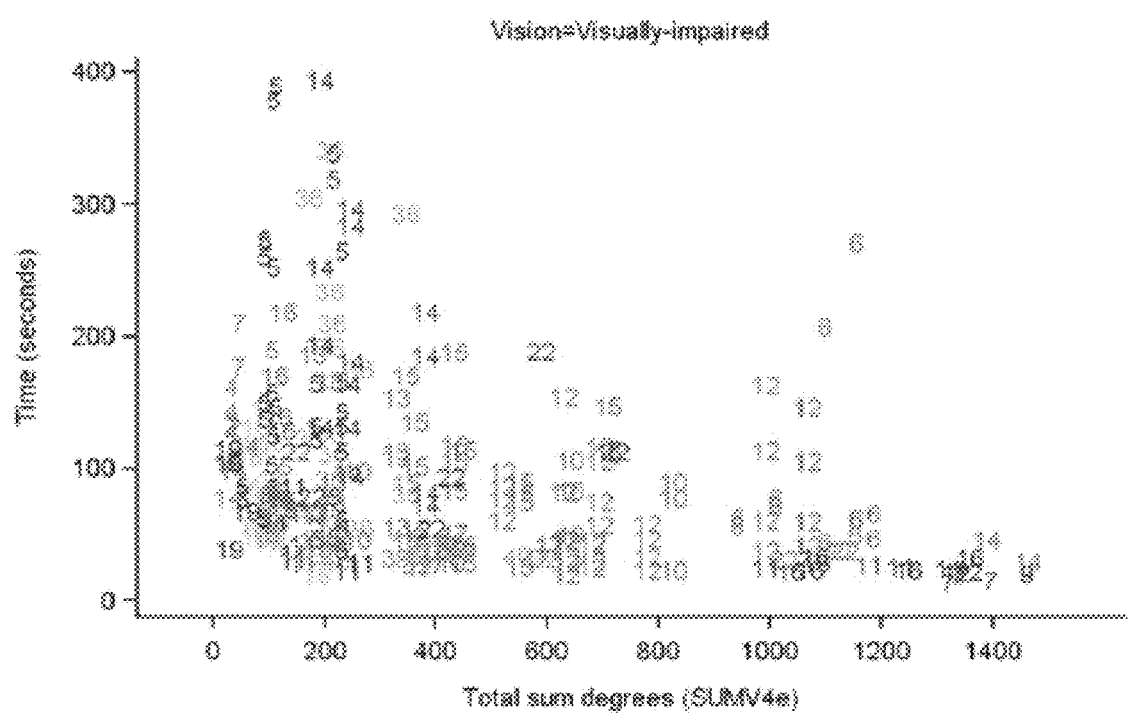

FIGS. 20A and 20B show data obtained during the mobility test validation study for Goldman visual fields (total sum degrees) versus time, by person, for normal-sighted and visually-impaired subjects, respectively.

Figure 21A:
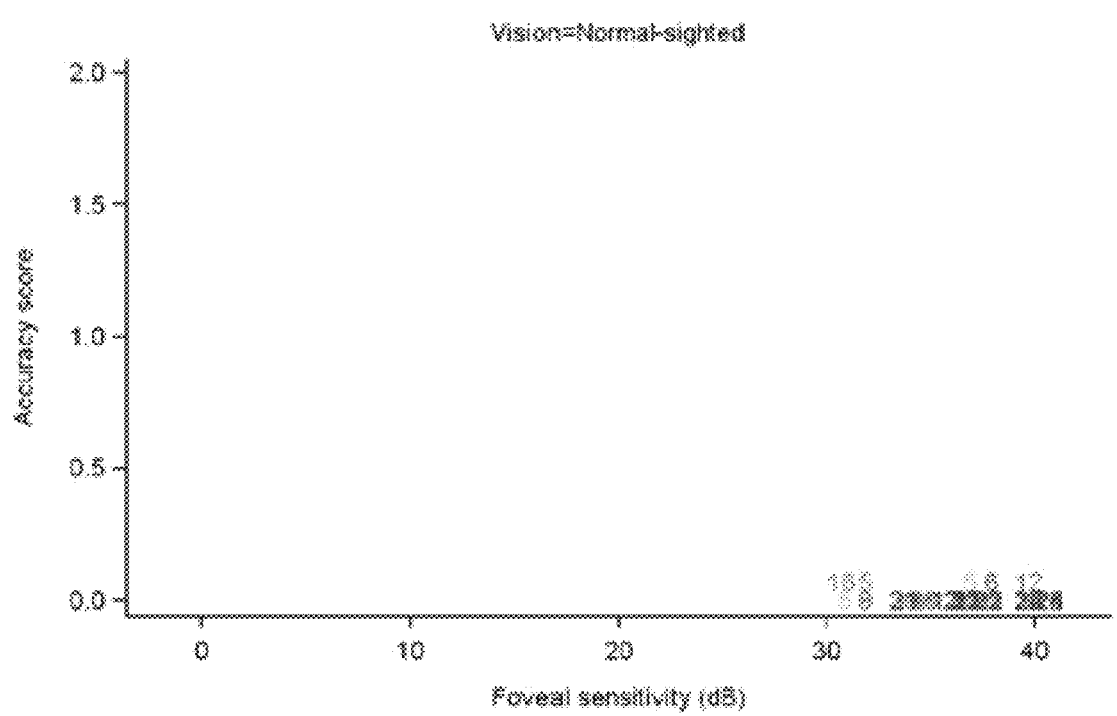
FIGS. 21A and 21B show data obtained during the mobility test validation study for Humphrey visual fields (foveal sensitivity) versus accuracy score, by person, for normal-sighted and visually-impaired subjects, respectively.
Figure 21B:
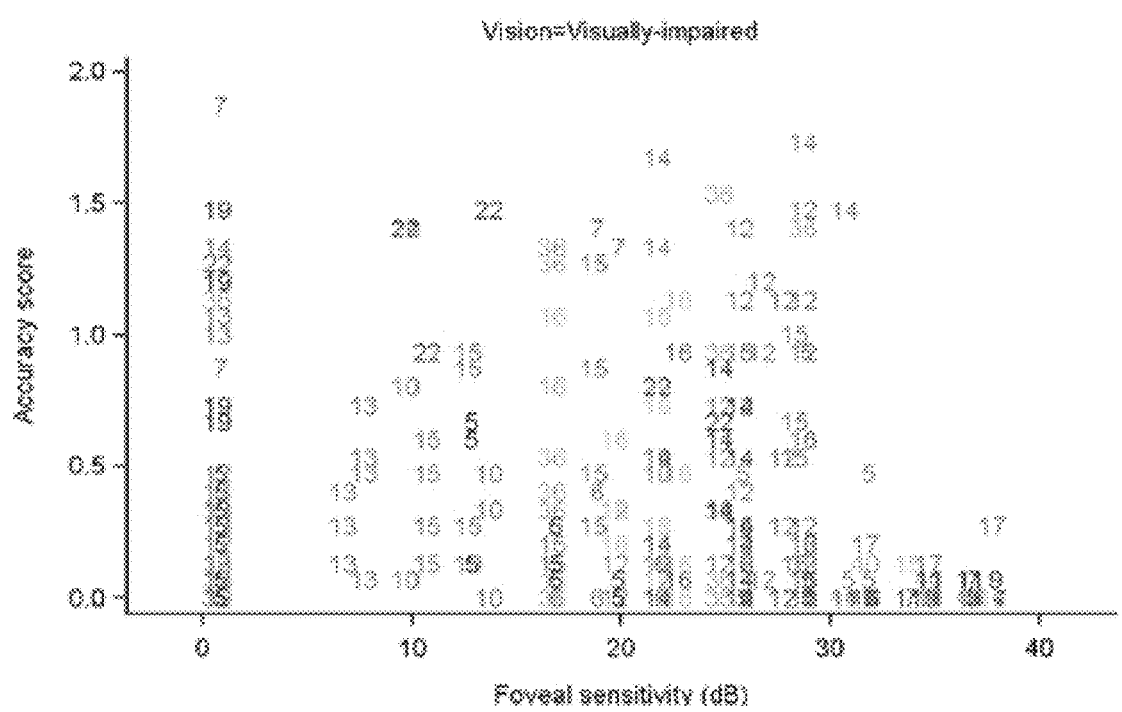

FIGS. 21A and 21B show data obtained during the mobility test validation study for Humphrey visual fields (foveal sensitivity) versus accuracy score, by person, for normal-sighted and visually-impaired subjects, respectively.

Figure 22A:
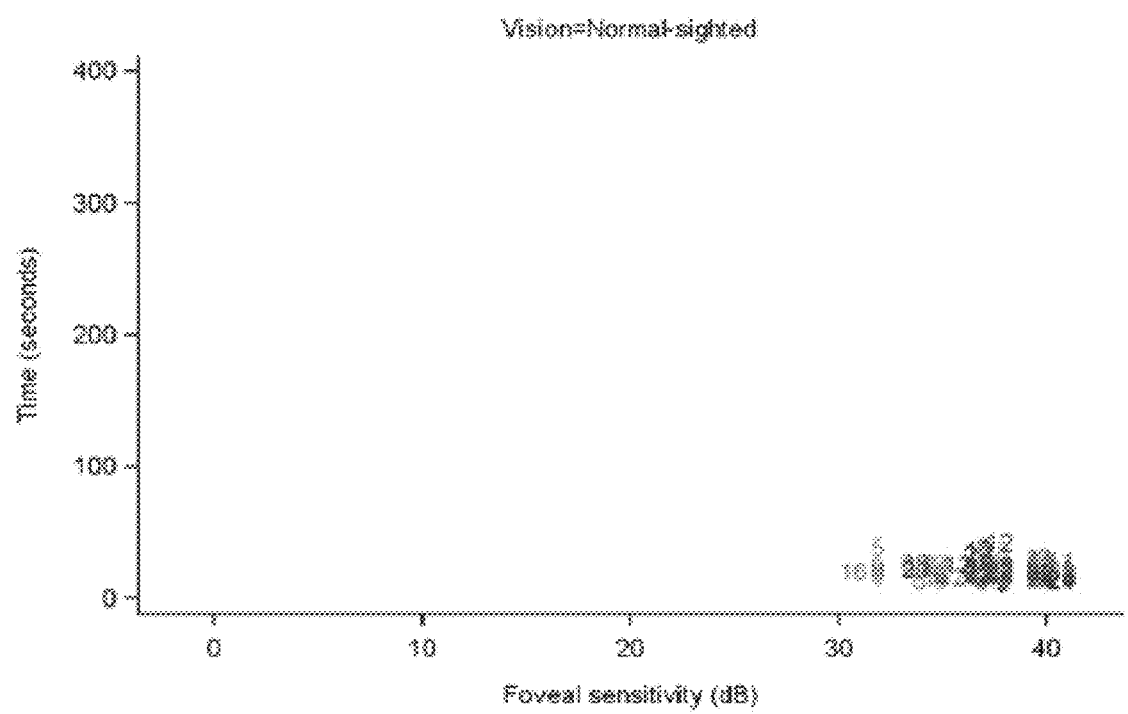
FIGS. 22A and 22B show data obtained during the mobility test validation study for Humphrey visual fields (foveal sensitivity) versus time, by person, for normal-sighted and visually-impaired subjects, respectively.
Figure 22B:
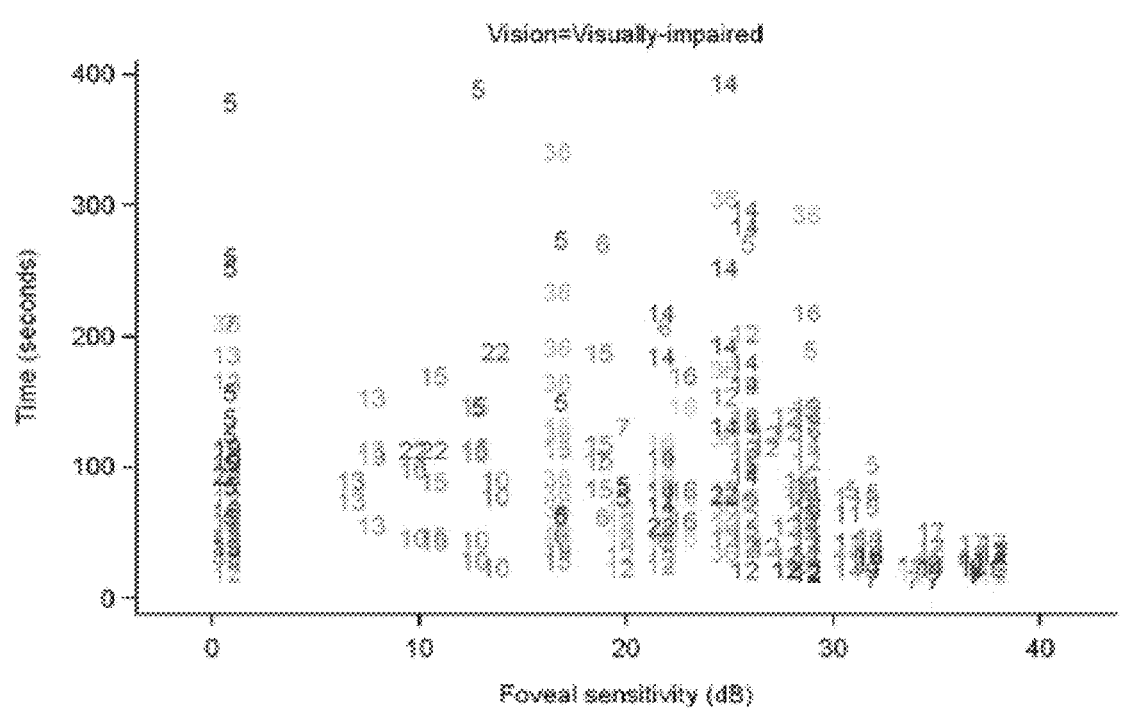

FIGS. 22A and 22B show data obtained during the mobility test validation study for Humphrey visual fields (foveal sensitivity) versus time, by person, for normal-sighted and visually-impaired subjects, respectively.

The visual function questionnaire (VFQ), which measures quality of life, is a series of questions with ratings on a standardized 0-10 scale. The summary score presented in FIGS. 23 and 24 is the average of the scores (unweighted) from all available questions. In FIGS. 23 and 24 consensus accuracy scores are used from each eye individually and from both eyes. There was a definite relationship between accuracy score and parent/guardian assessment among visually-impaired subjects.

Figure 23A:
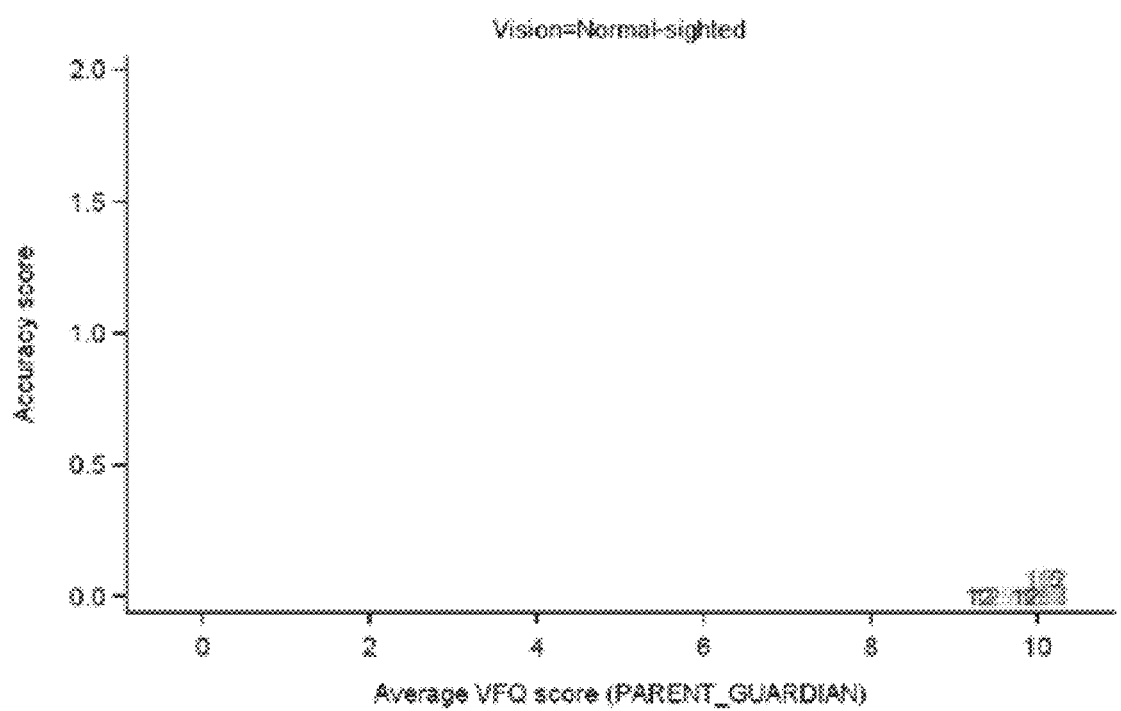
FIGS. 23A and 23B show data obtained during the mobility test validation study for visual function questionnaire averages versus accuracy score, based on parent/guardian assessments, for normal-sighted and visually-impaired subjects, respectively.
Figure 23B:
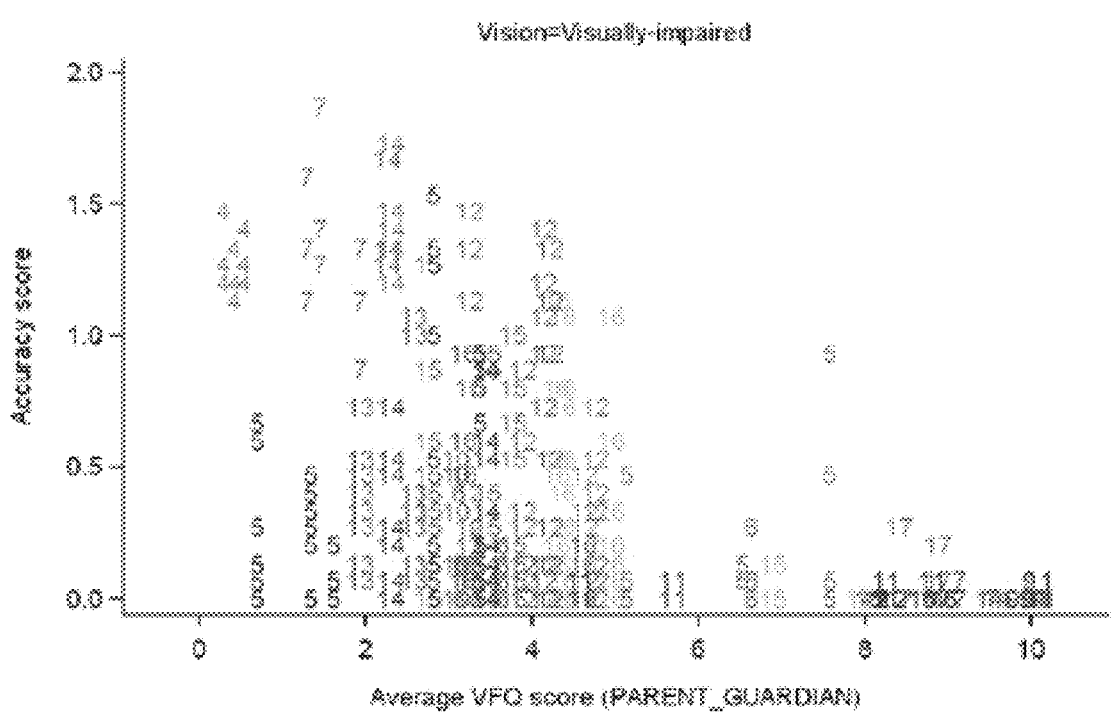

FIGS. 23A and 23B show data obtained during the mobility test validation study for visual function questionnaire averages versus accuracy score, based on parent/guardian assessments, for normal-sighted and visually-impaired subjects, respectively.

Figure 24A:
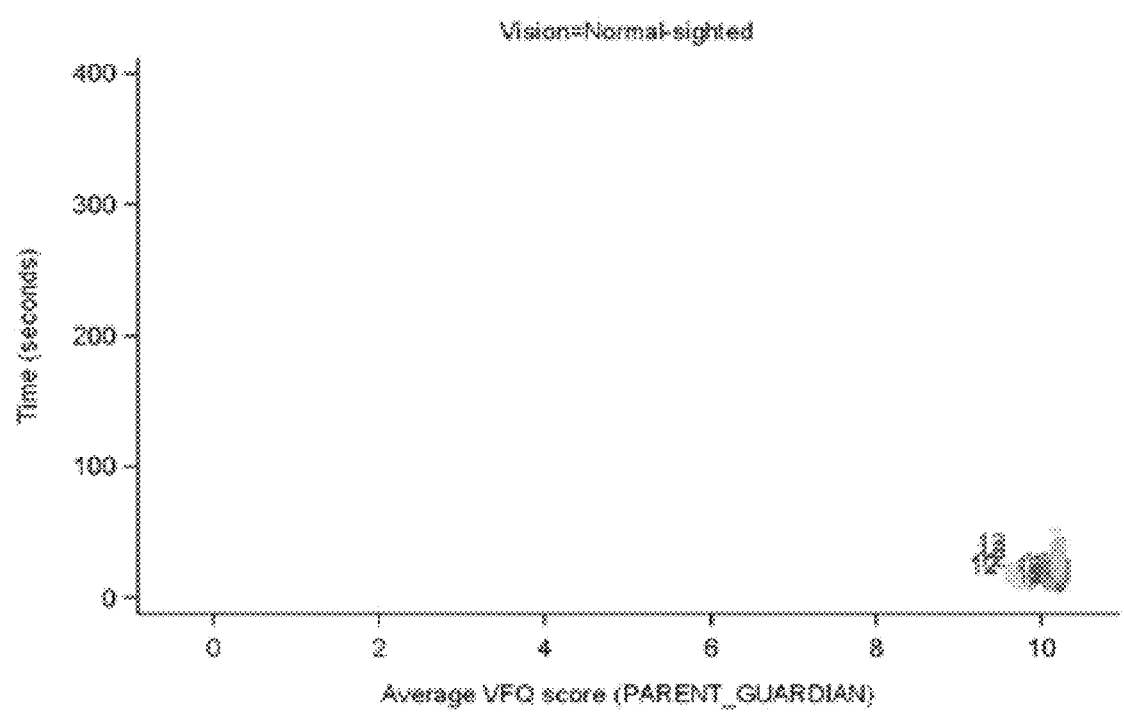
FIGS. 24A and 24B show data obtained during the mobility test validation study for visual function questionnaire averages versus accuracy score, based on parent/guardian assessments, for normal-sighted and visually-impaired subjects, respectively.
Figure 24B:
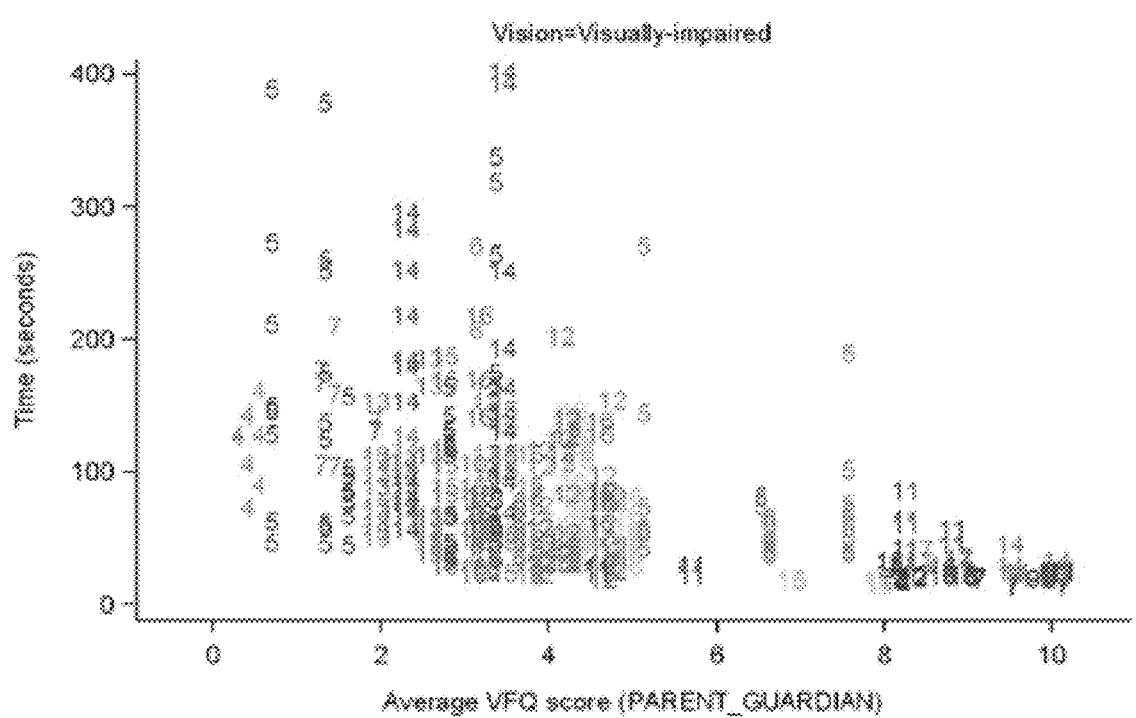

FIGS. 24A and 24B show data obtained during the mobility test validation study for visual function questionnaire averages versus accuracy score, based on parent/guardian assessments, for normal-sighted and visually-impaired subjects, respectively.

Although the disclosure has been described in detail for the purpose of illustration based on what is currently considered to be the most practical and exemplary implementations, it is to be understood that such detail is solely for that purpose and that the disclosure is not limited to the disclosed implementations, but, on the contrary, is intended to cover modifications and equivalent arrangements that are within the spirit and scope of the appended claims. For example, it is to be understood that the present disclosure contemplates that, to the extent possible, one or more features of any implementation can be combined with one or more features of any other implementation.

What is claimed is:

1. A method for performing a test of visual function and/or functional vision at varying luminance levels, the method comprising:
   selecting a first course of a plurality of courses for a subject, individual courses of the plurality of courses comprising a grid of tiles in a layout having a beginning point, at least one turn, at least one obstacle, and an ending point, wherein at least one of the tiles includes a directional arrow, and at least one of the tiles includes the at least one obstacle, the at least one obstacle comprising a physical object requiring avoidance, circumvention, traversal, and/or aversion;
   illuminating the first course with a first luminance level based on an estimated lower light sensitivity of the subject, the estimated lower light sensitivity being the lowest light sensitivity at which the subject can successfully navigate a preliminary course of the plurality of courses when the estimated lower light sensitivity is measured;
   indicating to a subject to perform a first run of the test, the test comprising, from the beginning point to the ending point, navigating the layout of the first course by walking around the at least one turn and avoiding the at least one obstacle; and
   determining whether the subject successfully completed the first course based on one or both of speed or accuracy, speed describing the time to complete the first course, accuracy describing avoidance of obstacles.

2. The method of claim 1, wherein the subject is required to rely on the subject's vision to navigate the first course.

3. The method of claim 1, wherein the subject has normal vision.

4. The method of claim 1, wherein the subject is suspected of having vision impairment or deficiency in one or both eyes.

5. The method of claim 1, wherein the subject is a candidate for one or both of ocular therapy, surgery or gene therapy of one or both eyes.

6. The method of claim 5, wherein one or both of the ocular therapy, surgery or the gene therapy is for treatment of Leber's congenital amaurosis (LCA) or choroideremia.

7. The method of claim 1, wherein the test is performed prior to the subject undergoing, or after the subject underwent, one or more of ocular therapy, surgery, or gene therapy of one or both eyes.

8. The method of claim 1, wherein the subject has received one or more, or all of, ocular therapy, surgery, or gene therapy.

9. The method of claim 1, wherein the test is performed after the subject underwent all of ocular therapy, surgery or gene therapy of one or both eyes.

10. The method of claim 1, wherein the test is repeated over a recovery period to measure improvement or decline associated with one or both or all of ocular therapy, surgery or gene therapy.

11. The method of claim 1, further comprising establishing the initial estimated lower light sensitivity cutoff.

12. The method of claim 1, further comprising dark-adapting the subject by prohibiting light to reach the subject's eyes for about thirty minutes to forty minutes.

13. The method of claim 1, wherein selection of the first course from among the plurality of courses is random.

14. The method of claim 1, wherein each of the plurality of courses has different layouts, individual ones of the layouts comprising the same number of turns and obstacles.

15. The method of claim 1, wherein individual ones of the plurality of courses comprise the grid of tiles, individual ones of the tiles being blank or including the directional arrow or the at least one obstacle.

16. The method of claim 1, wherein the at least one turn of the first course is marked by the directional arrow.

17. The method of claim 1, wherein the at least one turn of the first course includes a number of turns between one and five, inclusive.

18. The method of claim 1, wherein the at least one turn of the first course includes a number of turns between five and ten, inclusive.

19. The method of claim 1, wherein the at least one turn of the first course includes a number of turns between ten and fifteen, inclusive.

20. The method of claim 1, wherein the at least one turn of the first course includes a number of turns that is fifteen or more.

21. The method of claim 1, wherein the at least one obstacle includes one or more of an object placed adjacent to a path of a given course, a raised tile, a tile having a specific color indicative of obstacle, or an edge of a step.

22. The method of claim 1, wherein the at least one obstacle includes a first obstacle and a second obstacle, the first obstacle and the second obstacle differing in one or both of size or shape.

23. The method of claim 1, wherein a path of a given course that must be navigated to successfully complete the given course is between ten feet and twenty feet, inclusive.

24. The method of claim 1, wherein a path of a given course that must be navigated to successfully complete the given course is between twenty feet and fifty feet, inclusive.

25. The method of claim 1, wherein a path of a given course that must be navigated to successfully complete the given course is between fifty feet and one hundred feet, inclusive.

26. The method of claim 1, wherein a path of a given course that must be navigated to successfully complete the given course is one hundred feet or more.

27. The method of claim 1, wherein a path of a given course has a width of three feet or less.

28. The method of claim 1, wherein the path of a given course has a width of three feet or more.

29. The method of claim 1, wherein the first luminance level is at a sub-sensitivity level, the sub-sensitivity level being a luminance level below the estimated lower light sensitivity cutoff.

30. The method of claim 1, wherein the first luminance level is at a supra-sensitivity level, the supra-sensitivity level being a luminance level above the estimated lower light sensitivity cutoff.

31. The method of claim 1, wherein a room housing the first course is equipped with uniform lighting configured to provide about one lux to at least four hundred lux.

32. The method of claim 1, wherein the first luminance level is rounded to a nearest of a plurality of standardized luminance levels.

33. The method of claim 32, wherein the plurality of standardized luminance levels include one or more of one lux, four lux, ten lux, fifty lux, one hundred twenty five lux, two hundred fifty lux, or four hundred lux.

34. The method of claim 1, wherein the time to complete the first course equals a duration starting from a time of the indication to the subject to perform the first run to a time of completing the first course.

35. The method of claim 1, wherein the accuracy is quantified based on a number of collisions, a given collision being a forceful body contact with an object.

36. The method of claim 1, wherein the accuracy is quantified based on a number of times the subject moved off-course, the subject being off-course when both of the subject's feet are outside of a boundary of a path through a given course.

37. The method of claim 36, wherein the subject is guided back to the path responsive to being off-course.

38. The method of claim 1, further comprising assigning a score responsive to the subject completing the first run of the test, the score determined based on one or more of a number of collisions, a number of off-course events, a number of corrections provided by a test administrator, accuracy, or speed.

39. The method of claim 38, further comprising entering the score into a record associated with the subject.

40. The method of claim 1, further comprising performing subsequent runs of the test using other corresponding ones of the plurality of courses aside from the first course.

41. The method of claim 40, wherein there are five subsequent runs.

42. The method of claim 1, wherein the first run of the test is performed with one of (1) only the subject's right eye open, (2) only the subject's left eye open, or (3) both of the subject's eye open.

43. The method of claim 1, further comprising video recording the first run of the test using one or more cameras configured to capture video footage at the first luminance level.

44. The method of claim 1, wherein a layout of one of the individual ones of the plurality of courses comprises an individual layout illustrated in any of FIGS. 2-13.

45. The method of claim 1, further comprising performing a follow-up test by:
selecting a second course of the plurality of courses for the subject;
illuminating the second course with a second luminance level based on the estimated lower light sensitivity cutoff and whether the subject successfully completed the first course, the second luminance level being greater than, less than, or equal to the first luminance level;
indicating to the subject to perform a second run of the test, the test comprising, from the beginning point to the ending point, navigating the layout of the second course by walking around the at least one turn and avoiding the at least one obstacle; and
determining whether the subject successfully completed the second course based on one or both of speed or accuracy.

46. The method of claim 45, further comprising determining a lowest luminance level at which the subject can successfully complete the second course and a highest luminance level at which the subject cannot successfully complete the second course.

47. The method of claim 45, wherein the second luminance level is equal to the first luminance level or lower than the first luminance level responsive to a successful completion of the first course.

48. The method of claim 45, wherein the second luminance level is equal to the first luminance level or greater than the first luminance level responsive to an unsuccessful completion of the first course.

49. The method of claim 1, wherein the speed correlates with a visual acuity assessment score; a Goldman visual field assessment score; a Humphrey visual field assessment score; or a quality of life assessment score.

50. The method of claim 1, wherein the accuracy correlates with a visual acuity assessment score; a Goldman visual field assessment score; a Humphrey visual field assessment score; or a quality of life assessment score.

51. An apparatus configured for facilitating performance of a test of visual function and/or functional vision at varying luminance levels, the apparatus comprising:
a plurality of courses configured to facilitate performance of the test, individual courses of the plurality of courses comprising a grid of tiles in a layout having a beginning point, at least one turn, at least one obstacle, and an ending point, wherein at least one of the tiles includes a directional arrow, and at least one of the tiles includes the at least one obstacle, the at least one obstacle comprising a physical object requiring avoidance, circumvention, traversal, and/or aversion;
wherein performing the test comprises:
selecting a first course of the plurality of courses for a subject;
illuminating the first course with a first luminance level based on an estimated lower light sensitivity of the subject, the estimated lower light sensitivity being the lowest light sensitivity at which the subject can successfully navigate a preliminary course of the plurality of courses when the estimated lower light sensitivity is measured;
indicating to a subject to perform a first run of the test, the test comprising, from the beginning point to the ending point, navigating the layout of the first course by walking around the at least one turn and avoiding the at least one obstacle; and
determining whether the subject successfully completed the first course based on one or both of speed or accuracy, speed describing the time to complete the first course, accuracy describing avoidance of obstacles.

52. The apparatus of claim 51, wherein individual ones of the plurality of courses comprise a grid of tiles, individual ones of the tiles being blank or including a directional arrow or an obstacle.

53. The apparatus of claim 51, wherein the at least one turn of the first course is marked by the directional arrow.

54. The apparatus of claim 51, wherein the at least one turn of the first course includes a number of turns between one and five, inclusive.

55. The apparatus of claim 51, wherein the at least one turn of the first course includes a number of turns between five and ten, inclusive.

56. The apparatus of claim 51, wherein the at least one turn of the first course includes a number of turns between ten and fifteen, inclusive.

57. The apparatus of claim 51, wherein the at least one turn of the first course includes a number of turns that is fifteen or more.

58. The apparatus of claim 51, wherein the at least one obstacle includes one or more of an object placed adjacent to a path of a given course, a raised tile, a tile having a specific color indicative of obstacle, an edge of a step, or a reflective surface.

59. The apparatus of claim 51, wherein the at least one obstacle includes a first obstacle and a second obstacle, the first obstacle and the second obstacle differing in one or both of size or shape.

60. The apparatus of claim 51, wherein a path of a given course that must be navigated to successfully complete the given course is between ten feet and twenty feet, inclusive.

61. The apparatus of claim 51, wherein a path of a given course that must be navigated to successfully complete the given course is between twenty feet and fifty feet, inclusive.

62. The apparatus of claim 51, wherein a path of a given course that must be navigated to successfully complete the given course is between fifty feet and one hundred feet, inclusive.

63. The apparatus of claim 51, wherein a path of a given course that must be navigated to successfully complete the given course is one hundred feet or more.

64. The apparatus of claim 51, wherein a path of a given course has a width of three feet or less.

65. The apparatus of claim 51, wherein the path of a given course has a width of three feet or more.

66. The apparatus of claim 51, wherein a layout of one of the individual ones of the plurality of courses comprises an individual layout illustrated in any of FIGS. 2-13.

* * * * *

UNITED STATES PATENT AND TRADEMARK OFFICE
CERTIFICATE OF CORRECTION

PATENT NO.         : 10,448,823 B2
APPLICATION NO.    : 15/662153
DATED              : October 22, 2019
INVENTOR(S)        : High et al.

Page 1 of 1

It is certified that error appears in the above-identified patent and that said Letters Patent is hereby corrected as shown below:

In the Specification

At Column 1, after Line 12, add the "GOVERNMENT SUPPORT" paragraph, as follows:
-- GOVERNMENT SUPPORT
This invention was made with government support under EY023177 awarded by the National Institutes of Health. The government has certain rights in the invention. --

Signed and Sealed this
Twenty-ninth Day of December, 2020

Andrei Iancu
*Director of the United States Patent and Trademark Office*